(12) United States Patent
Crosbie et al.

(10) Patent No.: US 12,109,204 B2
(45) Date of Patent: Oct. 8, 2024

(54) METHODS FOR TREATING MUSCULAR DYSTROPHIES

(71) Applicant: The Regents of the University of California, Oakland, CA (US)

(72) Inventors: Rachelle H. Crosbie, Sherman Oaks, CA (US); Cynthia Shu, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 903 days.

(21) Appl. No.: 16/972,184

(22) PCT Filed: Jun. 5, 2019

(86) PCT No.: PCT/US2019/035537
§ 371 (c)(1),
(2) Date: Dec. 4, 2020

(87) PCT Pub. No.: WO2019/236677
PCT Pub. Date: Dec. 12, 2019

(65) Prior Publication Data
US 2021/0361635 A1    Nov. 25, 2021

Related U.S. Application Data

(60) Provisional application No. 62/680,728, filed on Jun. 5, 2018.

(51) Int. Cl.
| | |
|---|---|
| A61K 31/4439 | (2006.01) |
| A61K 31/137 | (2006.01) |
| A61K 31/40 | (2006.01) |
| A61K 31/404 | (2006.01) |
| A61K 31/427 | (2006.01) |
| A61K 31/439 | (2006.01) |
| A61K 31/4418 | (2006.01) |
| A61K 31/4422 | (2006.01) |
| A61K 31/498 | (2006.01) |
| A61K 31/522 | (2006.01) |
| A61K 31/525 | (2006.01) |
| A61K 31/565 | (2006.01) |
| A61K 31/7076 | (2006.01) |
| A61P 21/06 | (2006.01) |

(52) U.S. Cl.
CPC ........ *A61K 31/4439* (2013.01); *A61K 31/137* (2013.01); *A61K 31/40* (2013.01); *A61K 31/404* (2013.01); *A61K 31/427* (2013.01); *A61K 31/439* (2013.01); *A61K 31/4418* (2013.01); *A61K 31/4422* (2013.01); *A61K 31/498* (2013.01); *A61K 31/522* (2013.01); *A61K 31/525* (2013.01); *A61K 31/565* (2013.01); *A61K 31/7076* (2013.01); *A61P 21/06* (2018.01)

(58) Field of Classification Search
None
See application file for complete search history.

(56) References Cited

U.S. PATENT DOCUMENTS

| | | | | |
|---|---|---|---|---|
| 2008/0221027 | A1* | 9/2008 | Crosbie | A61K 31/70 435/320.1 |
| 2011/0158947 | A1* | 6/2011 | Jovanovic | A61P 9/10 548/496 |
| 2012/0083464 | A1* | 4/2012 | Villoslada Diaz | A61P 21/02 514/46 |
| 2014/0080896 | A1* | 3/2014 | Nelson | A61K 31/7105 506/10 |
| 2016/0250188 | A1* | 9/2016 | Bush | A61P 3/02 514/385 |

FOREIGN PATENT DOCUMENTS

| | | | | |
|---|---|---|---|---|
| CN | 104435880 A | 3/2015 | | |
| WO | WO-2013/033407 A2 | 3/2013 | | |
| WO | WO-2016114655 A1 * | 7/2016 | ........... | A61K 31/365 |
| WO | WO-2017035342 A2 * | 3/2017 | ........... | C12N 5/0657 |
| WO | WO-2019/236677 A1 | 12/2019 | | |

OTHER PUBLICATIONS

U.S. Appl. No. 18/025,747 filed Mar. 2023, Crosbie, Rachelle H.*
Triggle, "Calcium channel antagonists: Clinical uses—Past, present and future" Biochemical Pharmacology vol. 74 pp. 1-9 doi: 10.1016/j.bcp.2007.01.016 (Year: 2007).*
Guiraud et al., "Pharmacological advances for treatment in Duchenne muscular dystrophy," Current Opinion in Pharmacology, 34: 36-48 (2017).
International Search Report and Written Opinion for International Application No. PCT/US2019/035537 dated Sep. 23, 2019.
Parvatiyar et al., "Sarcospan Regulates Cardiac Isoproterenol Response and Prevents Duchenne Muscular Dystrophy-Associated Cardiomyopathy," Journal of the American Heart Association, 4(12):e002481 (2015).
Batchelor et al., "Sparks, signals and shock absorbers: how dystrophin loss causes muscular dystrophy," Trends in Cell Biology, 16(4): 198-205 (2006).
Blat et al., "Drug discovery of therapies for duchenne muscular dystrophy," Journal of Biomolecular Screening, 20(10): 1189-1203 (2015).
Extended European Search Report for EP Application No. 19815502.0 dated Jan. 27, 2022.

(Continued)

*Primary Examiner* — Eric Olson
(74) *Attorney, Agent, or Firm* — Foley Hoag LLP; David P. Halstead

(57) ABSTRACT

Provided herein are methods for treating and preventing a disease related to diminution or dysfunction of a dystrophin-related complex in a subject in need thereof, comprising administering to the subject a compound that increases sarcospan. Also provided herein are pharmaceutical compositions comprising a compound that increases sarcospan, or a pharmaceutically acceptable salt or ester thereof, useful for the treatments described herein.

7 Claims, 13 Drawing Sheets

Specification includes a Sequence Listing.

(56) References Cited

OTHER PUBLICATIONS

Marshall et al., "Sarcospan: a small protein with large potential for Duchenne muscular dystrophy," Skeletal Muscle, 3(1): 13 pages (2013).
Marshall et al., "The potential of sarcospan in adhesion complex replacement therapeutics for the treatment of muscular dystrophy," The FEBS Journal, 280(17): 4210-4229 (2013).

* cited by examiner

METHODS FOR TREATING MUSCULAR DYSTROPHIES

RELATED APPLICATIONS

This application is a § 371 national-stage application based on PCT/US19/35537, filed Jun. 5, 2019 which claims a right of priority from and the benefit of an earlier filing date of U.S. Provisional Application No. 62/680,728, filed on Jun. 5, 2018, the specifications of which are is hereby incorporated by reference herein in their entireties.

REFERENCE TO A SEQUENCE LISTING

This application contains a Sequence Listing in ASCII text format and is incorporated by reference in its entirety. Said ASCII copy, created on Jun. 10, 2024, is named UCH-15001_SL.txt and is 9,711 bytes in size.

GOVERNMENT SUPPORT

This invention was made with government support under Grant Numbers HL126204, AR048179, and AR065972, awarded by the National Institutes of Health. The Government has certain rights in the invention.

BACKGROUND

Muscular dystrophies span approximately thirty inherited disorders characterized by weakness and wasting away of muscle tissue, with or without the breakdown of nerve tissue. There are nine main types of muscular dystrophy, each of which involve an eventual loss of strength, increasing disability, and possible physical deformity. Duchenne muscular dystrophy (DMD), is the most well-known type of muscular dystrophy, affecting approximately 1 in every 5,700 male births worldwide. DMD is caused by loss of sarcolemma adhesion to the extracellular matrix.

The development of therapies for DMD is gaining momentum with the recent accelerated approval of eteplirsen in 2016 and the increased private sector funding of rare disease programs. However, the existing FDA approved drugs for DMD are not sufficient to substantially slow disease progression. While corticosteroids dampen inflammation and extend ambulation by several years, they do not address adhesion complex and membrane stability deficiencies. The antisense oligonucleotide exon skipping therapy eteplirsen increases truncated dystrophin protein production, but is only applicable to the approximately 14% of DMD patients with mutations amenable to exon 51 skipping. There remains a need to identify more robust treatments for muscular dystrophy and other muscle wasting diseases.

SUMMARY

In certain aspects, the present disclosure provides methods for treating or preventing diseases related to dysfunction of a dystrophin-related complex in a subject in need thereof, comprising administering to the subject a compound that increases the expression of sarcospan, e.g., thereby ameliorating one or more symptoms of the disease.

Sarcospan is a transmembrane protein found in skeletal, smooth, and cardiac muscle, that is associated with several adhesion complexes including integrin, the dystrophin-glycoprotein complex, and the utrophin-glycoprotein complex. Overexpression of sarcospan has been shown to ameliorate disease symptoms and improve skeletal and cardiac muscle, as well as respiratory dysfunction in several relevant mouse models of DMD.

In some aspects, methods of treating or preventing a disease related to dysfunction of a dystrophin-related complex in a subject in need thereof include administering to the subject a compound that increases the expression of sarcospan. The disease related to dysfunction of a dystrophin-related complex, in various embodiments, is muscular dystrophy (e.g., Becker muscular dystrophy (BMD), congenital muscular dystrophy (CMD), Duchenne muscular dystrophy (DMD), distal muscular dystrophy, Emery-Dreifuss muscular dystrophy, facioscapulohumeral muscular dystrophy, limb-girdle muscular dystrophy, myotonic dystrophy, oculopharyngeal muscular dystrophy). The compound, in some embodiments, is 2-[3-(1,3-Dihydro-1,3,3-trimethyl-2H-indol-2-ylidene)-1-propenyl]-3-ethyl-benzothiazolium iodide (AC-93253); 1-Azabicyclo[2.2.2]oct-3-yl acetate (aceclidine); 2-amino-9-(2-hydroxyethoxymethyl)-3H-purin-6-one (acyclovir); 1H-benzo[g]pteridine-2,4-dione (alloxazine); methyl N-[(E)-(1-hydroxy-4-oxidoquinoxalin-4-ium-2-ylidene)methyl]iminocarbamate (carbadox); (3Z)-3-[(3,5-dibromo-4-hydroxyphenyl)methylidene]-5-iodo-1H-indol-2-one (GW5074); 4-[1-hydroxy-2-(propan-2-ylamino)ethyl]benzene-1,2-diol (isoproterenol); (2R,3R,4S,5S)-2-(6-aminopurin-9-yl)-5-(methylsulfanylmethyl)oxolane-3,4-diol (methylthioadenosine); N-[(1-butylpyrrolidin-2-yl)methyl]-4-cyano-1-methoxynaphthalene-2-carboxamide (nafadotride); (8R,9S,10R,13 S,14S,17S)-17-hydroxy-13-methyl-2,6,7,8,9,10,11,12,14,15,16,17-dodecahydro-1H-cyclopenta[a]phenanthren-3-one (nandrolone); 5-O-ethyl 3-O-methyl 4-(2,3-dichlorophenyl)-2,6-dimethyl-1,4-dihydropyridine-3,5-dicarboxylate (felodipine); 3-O-methyl 5-O-propan-2-yl 4-(2,1,3-benzoxadiazol-4-yl)-2,6-dimethyl-1,4-dihydropyridine-3,5-dicarboxylate (isradipine); diethyl 2,6-dimethyl-4-[2-[(E)-3-[(2-methylpropan-2-yl)oxy]-3-oxoprop-1-enyl]phenyl]-1,4-dihydropyridine-3,5-dicarboxylate (lacidipine); dimethyl 2,6-dimethyl-4-(2-nitrophenyl)-1,4-dihydropyridine-3,5-dicarboxylate (nifedipine); 3-O-methyl 5-O-propan-2-yl 2-cyano-6-methyl-4-(3-nitrophenyl)-1,4-dihydropyridine-3,5-dicarboxylate (nilvadipine); or a pharmaceutically acceptable salt or ester thereof. In some embodiments, the sarcospan mRNA transcript, sarcospan protein level, or both the sarcospan mRNA transcript and sarcospan protein level are increased. The subject can be a human.

In some aspects, for any of the embodiments disclosed herein, a compound that increases the expression of sarcospan (or a composition including such a compound) for use in treatment or prevention of a disease related to dysfunction of a dystrophin-related complex in a subject in need thereof is disclosed. Also disclosed, in some aspects for any of the embodiments disclosed herein, is the use of a compound that increases the expression of sarcospan in the manufacture of a medicament for treatment or prevention of a disease related to dysfunction of a dystrophin-related complex.

DETAILED DESCRIPTION

Figure 1:
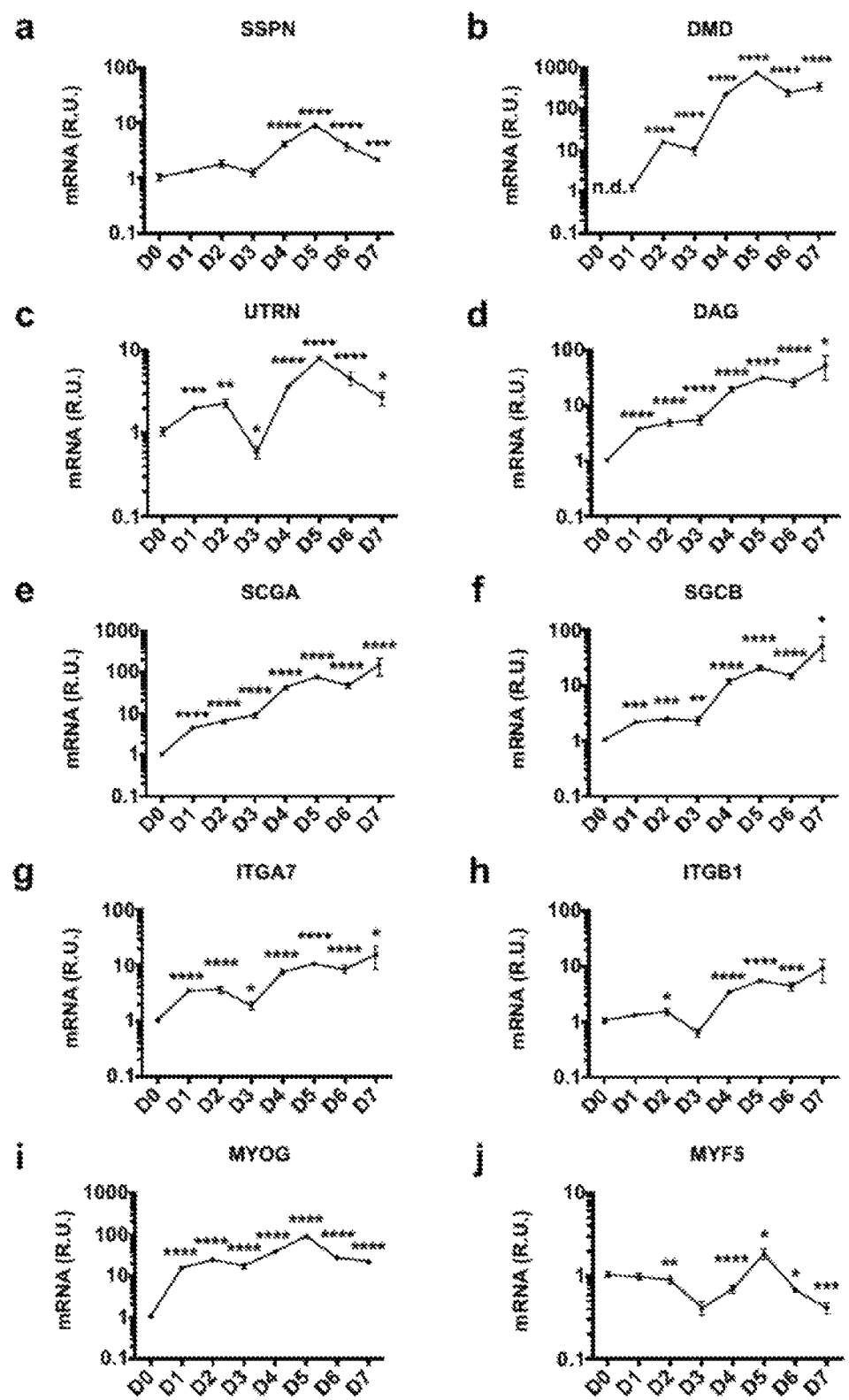
FIG. 1 has ten panels, a-j, which show that the individual components of muscle adhesion complexes increase during C2C12 differentiation. Confluent C2C12 myoblasts (day 0, D0) were switched from proliferation to differentiation media and harvested daily for seven days (D1 to D7). Individual genes encoding protein components of the three major adhesion complexes (DGC, UGC, and α7β1D-integrin complex) were investigated, including: (a) SSPN, sarcospan; (b) DMD, dystrophin; (c) UTRN, utrophin; (d) DAG, dystroglycan, (e) SCGA, α-sarcoglycan; (f) SCGB, β-sarcoglycan; (g) ITGA7, α7 integrin; and (h) ITGB1, (β1D integrin. Analysis of myogenin (MYOG, i) and myogenic factor 5 (MYF5, j) are provided as markers for muscle cell differentiation. For DMD D0, n.d. (no data) indicates no detectable expression. Gene expression was calculated using the ddCt method and normalized to β-actin with day 0 (myoblast) values serving as the calibrator sample (n=3). R.U.: relative units. Results are plotted on a log scale. *$p<0.05$, $p<0.01$, *$p<0.001$, ****$p<0.0001$.

The heterogeneity of mutations and difficulty of delivery to muscle are major challenges to the development of therapies to treat DMD. There is an urgent need for improved therapies that can overcome these challenges. Sarcospan (SSPN) reduces the pathology of muscular dystrophy in the DMD murine model by increasing membrane localization of the utrophin-glycoprotein complex (UGC) and α7β1D-integrin adhesion complexes, effectively increasing laminin binding to compensate for the loss of dystrophin.

Development of small molecule therapies that increase SSPN expression may lead to standalone or combinatorial therapies to treat DMD and other forms of muscular dystrophy caused by deficits in membrane proteins. Small molecule therapies are ideal due to their ability to bypass the limitations of delivery and immune responses seen with viral and cell-based methods.

In certain aspects, the present disclosure provides methods for treating or preventing a disease related to dysfunction of a dystrophin-related complex in a subject in need thereof, comprising administering to the subject a compound that increases the expression of sarcospan, whereby symptoms of the disease are reduced. In preferred embodiments, the disease related to dysfunction of a dystrophin-related complex is muscular dystrophy. The muscular dystrophy may be Becker muscular dystrophy (BMD), congenital muscular dystrophy (CMD), Duchenne muscular dystrophy (DMD), distal muscular dystrophy, Emery-Dreifuss muscular dystrophy, facioscapulohumeral muscular dystrophy, limb-girdle muscular dystrophy, myotonic dystrophy, or oculopharyngeal muscular dystrophy. In certain embodiments, the muscular dystrophy is Duchenne muscular dystrophy.

In some embodiments, the compound is a retinoic acid receptor-a agonist, such as 2-[3-(1,3-Dihydro-1,3,3-trimethyl-2H-indol-2-ylidene)-1-propenyl]-3-ethyl-benzothiazolium iodide (AC-93253), or a pharmaceutically acceptable salt or ester thereof. In other embodiments, the compound is a muscarinic receptor agonist. For example, the compound can be 1-Azabicyclo[2.2.2]oct-3-yl acetate (aceclidine), or a pharmaceutically acceptable salt or ester thereof. In yet other embodiments, the compound is a herpesvirus DNA polymerase inhibitor (e.g., 2-amino-9-(2-hydroxyethoxymethyl)-3H-purin-6-one (acyclovir), or a pharmaceutically acceptable salt or ester thereof.

The compound may be a selective A2b adenosine receptor antagonist, such as 1H-benzo[g]pteridine-2,4-dione (alloxazine), or a pharmaceutically acceptable salt or ester thereof. In some embodiments, the compound may be a veterinary antibiotic. For example, the compound may be methyl N-[(E)-(1-hydroxy-4-oxidoquinoxalin-4-ium-2-ylidene)methyl]iminocarbamate (carbadox), or a pharmaceutically acceptable salt or ester thereof.

In some embodiments, the compound is an L-type calcium channel blocker. For example, the compound may be 5-O-ethyl 3-O-methyl 4-(2,3-dichlorophenyl)-2,6-dimethyl-1,4-dihydropyridine-3,5-dicarboxylate (felodipine), 3-O-methyl 5-O-propan-2-yl 4-(2,1,3-benzoxadiazol-4-yl)-2,6-dimethyl-1,4-dihydropyridine-3,5-dicarboxylate (isradipine), diethyl 2,6-dimethyl-4-[2-[(E)-3-[(2-methylpropan-2-yl)oxy]-3-oxoprop-1-enyl]phenyl]-1,4-dihydropyridine-3,5-dicarboxylate (lacidipine), dimethyl 2,6-dimethyl-4-(2-nitrophenyl)-1,4-dihydropyridine-3,5-dicarboxylate (nifedipine), 3-O-methyl 5-O-propan-2-yl 2-cyano-6-methyl-4-(3-nitrophenyl)-1,4-dihydropyridine-3,5-dicarboxylate (nilvadipine), or pharmaceutically acceptable salts or esters thereof.

In other embodiments, the compound is a cRaf1 kinase inhibitor, such as (3Z)-3-[(3,5-dibromo-4-hydroxyphenyl)methylidene]-5-iodo-1H-indol-2-one (GW5074), or a pharmaceutically acceptable salt or ester thereof. The compound may be a sympathomimetic amine (e.g., 4-[1-hydroxy-2-(propan-2-ylamino)ethyl]benzene-1,2-diol (isoproterenol), or a pharmaceutically acceptable salt or ester thereof. The compound may be a P2 purinoceptor agonist. For example, the compound may be (2R,3R,4S,5S)-2-(6-aminopurin-9-yl)-5-(methylsulfanylmethyl)oxolane-3,4-diol (methylthioadenosine), or a pharmaceutically acceptable salt or ester thereof.

The compound may be a dopamine receptor antagonist, such as N-[(1-butylpyrrolidin-2-yl)methyl]-4-cyano-1-methoxynaphthalene-2-carboxamide (nafadotride), or a pharmaceutically acceptable salt or ester thereof. Alternatively, the compound may be an anabolic androgenic steroid. For example, the compound may be (8R,9S,10R,13 S,14S,17S)-17-hydroxy-13-methyl-2,6,7,8,9,10,11,12,14,15,16,17-dodecahydro-1H-cyclopenta[a]phenanthren-3-one (nandrolone), or a pharmaceutically acceptable salt or ester thereof.

In some embodiments, sarcospan mRNA transcript is increased. Additionally or alternatively, the sarcospan protein level is increased.

In preferred embodiments, the subject is human.

In certain aspects, provided herein are methods for treating or preventing muscular dystrophy in a subject in need thereof, comprising administering to the subject a pharmaceutical composition comprising a compound that increases the expression of sarcospan.

Definitions

As used herein the specification, "a" or "an" may mean one or more. As used herein in the claim(s), when used in conjunction with the word "comprising," the words "a" or "an" may mean one or more than one. As used herein, "another" may mean at least a second or more.

As used herein, the term "biomarker" is anything that can be used as an indicator of a particular physiological state of an organism. For example, a biomarker can be the level(s) of a particular by-product, metabolite, mRNA or protein associated with a particular physiological state.

The phrase "pharmaceutically-acceptable carrier" as used herein means a pharmaceutically-acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "preventing" is art-recognized, and when used in relation to a condition, such as a local recurrence, is well understood in the art, and includes administration of a composition which reduces the frequency of, or delays the onset of, symptoms of a medical condition in a subject relative to a subject which does not receive the composition. Thus, prevention of a disease related to dysfunction of a dystrophin-related complex includes, for example, reducing problems in the joints and spine while increasing muscle strength in a population of patients receiving a prophylactic treatment relative to an untreated control population, and/or delaying the progression of the disease in a treated population versus an untreated control population, e.g., by a statistically and/or clinically significant amount.

The term "prophylactic" or "therapeutic" treatment is art-recognized and includes administration to the host of one or more of the subject compositions. If it is administered prior to clinical manifestation of the unwanted condition (e.g., disease or other unwanted state of the host animal), then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof.

The term "subject" refers to a mammal, including, but not limited to, a human or non-human mammal, such as a bovine, equine, canine, ovine, or feline.

As used herein, the term "treating" or "treatment" includes reversing, reducing, or arresting the symptoms, clinical signs, and underlying pathology of a condition in a manner to improve or stabilize a subject's condition.

Therapeutic Methods

Provided herein are methods of treating or preventing a disease related to dysfunction of a dystrophin-related complex in a subject by administering to the subject a therapeutically effective amount of compound that increases the expression of sarcospan. In certain embodiments, the methods relate to treating muscular dystrophy, specifically Duchenne muscular dystrophy. Also provided are methods for treating muscular dystrophy in a subject by administering to the subject a therapeutically effective amount of a pharmaceutical composition disclosed herein.

Compositions

In some aspects, the invention relates to a pharmaceutical composition comprising a compound that increases the expression of sarcospan. The composition may comprise a pharmaceutically acceptable carrier. The pharmaceutical composition disclosed herein may be delivered by any suitable route of administration, including orally, buccally, sublingually, parenterally, and rectally, as by powders, ointments, drops, liquids, gels, tablets, capsules, pills, or creams. In certain embodiments, the pharmaceutical compositions are delivered systemically (e.g., via oral administration). In some embodiments, the compositions disclosed herein are delivered intravenously.

Actual dosage levels of the active ingredients in the pharmaceutical compositions may be varied so as to obtain an amount of the active ingredient which is effective to achieve the desired therapeutic response for a subject, composition, and mode of administration, without being toxic to the subject.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the subject being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds employed in the pharmaceutical composition at levels lower than that required in order to achieve the desired therapeutic effect and gradually increase the dosage until the desired effect is achieved.

EXEMPLIFICATION

Example 1: Materials and Methods

Gene Expression Analysis

RNA from myotubes treated for 48 hours was extracted from cells using Trizol-based (Thermo Fisher Scientific) phase separation. RNA concentrations were determined using a NanoDrop 1000 (Thermo Fisher Scientific) and 750 ng of RNA in a 20 µl reaction was reverse transcribed using iScript cDNA synthesis (Bio-Rad) with the following cycling conditions: 25° C. for 5 minutes, 42° C. for 30 minutes, 85° C. for 5 minutes. For quantitative PCR, SsoFast EvaGreen Supermix (Bio-Rad), 400 nM of each optimized forward and reverse primer (for primer descriptions see Table 1), and cDNA corresponding to 37.5 ng RNA were used to amplify cDNA measured by Applied Biosystems 7300 (Thermo Fisher Scientific) with the following reaction conditions: 55° C. for 2 minutes, 95° C. for 2 minutes, 40 cycles of 95° C. for 10 seconds and 62° C. for 30 seconds, and dissociation stage. Each sample was run in triplicate. Data was analyzed using the ddCT method and normalized to reference gene, GAPDH or β-actin, with vehicle-treated samples serving as the calibrator (relative expression of vehicle control=1).

Table 1 shows the primers used for gene expression analysis (SEQ ID NOS 1-24, respectively, in order of appearance). Primers were optimized by standard curve method using cDNA corresponding to 75 ng RNA, diluted 2-fold. AE: amplification efficiency, calculated using the equation AE=[10(−1/slope)]/−1. SSPN, sarcospan; DMD, dystrophin; UTRN, utrophin; DAG, dystroglycan, SCGA, α-sarcoglycan; SCGB, β-sarcoglycan; ITGA7, α7 integrin; ITGB1, β1D integrin; MYOG, myogenin; MYF5, myogenic factor 5; ACTB, β-actin; GADPH, glyceraldehyde 3-phosphate dehydrogenase.

TABLE 1

| PRIMER | SEQUENCE (5' → 3') | LOCATION | AMPLICON LENGTH | AE |
|---|---|---|---|---|
| UTRN F | GTATGGGGACCTTGAAGCCAG | exons 1-2 | 125 BP | 118% |
| UTRN R | ATCGAGCGTTTATCCATTTGGT | | | |
| DMD F | GGAAAGCAACACATAGACAACCT | exons 3-4 | 65BP | 111% |
| DMD R | GGGCATGAACTCTTGTAGATCC | | | |
| ITGA7 F | GATCGTCCGAGCCAACATCACA | exons 23-24 | 165 BP | 115% |
| ITGA7 R | CTAACAGCCCAGCCAGCACT | | | |
| ITGB1 F | ATGCCAAATCTTGCGGAGAAT | exons 3-4 | 209 BP | 105% |
| ITGB1 R | TTTGCTGCGATTGGTGACATT | | | |
| DAG1 F | CAGACGGTACGGCTGTTGTC | exons 3-4 | 126 BP | 112% |
| DAG1 R | AGTGTAGCCAAGACGGTAAGG | | | |
| SGCA F | GCAGCAGTAACTTGGATACCTC | exons 2-3 | 113 BP | 117% |
| SGCA R | AAAGGATGCACAAACACACGA | | | |
| SGCB F | AGCACAACAGCAATTTCAAAGC | exon 2 | 112 BP | 100% |
| SGCB R | AGGAGGACGATCACGCAGAT | | | |
| SSPN F | TGCTAGTCAGAGATACTCCGTTC | exons 1-2 | 103 BP | 94% |
| SSPN R | GTCCTCTCGTCAACTTGGTATG | | | |
| MYOG F | GAGATCCTGCGCAGCGCCAT | exon 1 | 97 BP | 107% |
| MYOG R | CCCCGCCTCTGTAGCGGAGA | | | |
| MYF5 F | AAGGCTCCTGTATCCCCTCAC | exon 1 | 249 BP | 117% |
| MYF5 R | TGACCTTCTTCAGGCGTCTAC | | | |
| ACTB F | TCCTGACCCTGAAGTACCCCAT | exons 1-2 | 131 BP | 104% |
| ACTB R | CTCGGTGAGCAGCACAGGGT | | | |
| GAPDH F | CAACTTTGGCATTGTGGAAGG | exons 4-5 | 135 BP | 92% |
| GAPDH R | GTGGATGCAGGGATGATGTT | | | |

Molecular Cloning of SSPN Reporter Plasmids

The SSPN promoter region was predicted using publically available data on UCSC genome browser (http://genome.ucsc.edu/). Using the GRCh37/hg19 assembly, gene regulatory elements of the cardiac and skeletal muscle-specific SSPN transcript variant 1 (NM_005086.4) of the human PureLink Quick Plasmid Miniprep (Life Technologies) and subjected to DNA sequencing (Laragen Inc.) using the primers in Table 2a or 2b to confirm presence and accuracy of the SSPN promoter region. Select bacterial cultures were grown in large cultures and collected for plasmid purification using the Plasmid Maxi Kit (Qiagen).

TABLE 2a (SEQ ID NOS 25-31, respectively, in order of appearance)

| PRIMER | SEQUENCE (5' → 3') | LOCATION |
| --- | --- | --- |
| Universal forward primer | GTGTAGATCTCAGGTGGGTGTCCTGGTATAA | 2 kb upstream of hSSPN TSS |
| EGFP construct reverse primer | GTGTAAGCTTCTCCTCCCCGCACTCCTT | Exon 1 of hSSPN |
| Luciferase construct reverse primer | GTGTAAGCTTGCTCCTCCCCGCACTCCTT | Exon 1 of hSSPN |
| EGFP sequencing forward primer 1 | ATAACCGTATTACCGCCATGCATTA | 25 bp upstream of hSSPN promoter |
| Luciferase sequencing forward primer 1 | CAGAACATTTCTCTGGCCTAACTGG | 35 bp upstream of hSSPN promoter |
| Universal sequencing forward primer 2 | CTCTAAGTGCTACTGAGTAGAGGTA | 600 bp within hSSPN promoter |
| Universal sequencing forward primer 3 | CAGCCACTTGGAGACTGAGGAGAGA | 1200 bp within hSSPN promoter |

TABLE 2b (SEQ ID NOS 32-36, respectively, in order of appearance)

| PRIMER | SEQUENCE (5' → 3') | LOCATION |
| --- | --- | --- |
| EGFP construct forward primer | GTGTAGATCTCAGGTGGGTGTCCTGGTATAA | 2 kb upstream of hSSPN TSS |
| EGFP construct reverse primer | GTGTAAGCTTCTCCTCCCCGCACTCCTT | Exon 1 of hSSPN |
| EGFP sequencing forward primer 1 | ATAACCGTATTACCGCCATGCATTA | 25 bp upstream of hSSPN promoter |
| EGFP sequencing forward primer 2 | CTCTAAGTGCTACTGAGTAGAGGTA | 600 bp within hSSPN promoter |
| EGFP sequencing forward primer 3 | CAGCCACTTGGAGACTGAGGAGAGA | 1200 bp within hSSPN promoter |

SSPN gene (NG_012011.2) were identified. H2K4me3 marks, DNase hypersensitivity regions, and ChIP-seq data showing transcription factor binding locations from human skeletal muscle cultures indicated the promoter region to be upstream of exon 1 and within exon 1. A 2 kb region encompassing the human SSPN promoter was amplified from human genomic DNA (Bioline) using Phusion High Fidelity DNA Polymerase (New England Biolabs) with the primers indicated in Table 2a or 2b. The primers contained leader sequences and restriction sites for BglII (AGATCT) or HindIII (TTCGAA). The PCR products were purified using PureLink HiPure Plasmid DNA Purification kit (Life Technologies) and digested with BglII and HindIII in NEBuffer 3.1 (New England Biolabs). The 2 kb digested PCR products were electrophoresed on agarose gels, excised, and purified using the Zymoclean Gel DNA Recovery Kit (Zymo Research). T4 DNA ligase (Invitrogen) was used to ligate PCR products with promoter-less reporter plasmids, pmEGFP-1 (Addgene, plasmid #36409) or pgl4.17 (Promega), prepared by digestion with BglII and HindIII. The plasmid constructs were linearized with BglII, which digested the region upstream of the SSPN promoter. The linearized plasmids were purified and used to transform One Shot TOP10 chemically competent E. coli (Thermo Fisher) grown on agar containing the appropriate antibiotic. Individual colonies were confirmed by colony PCR to contain the SSPN promoter construct and inoculated in liquid culture overnight. The plasmids were purified using Table 2b shows the primers used for reporter construct cloning and sequencing. Cloning was optimized for human sarcospan (SSPN) gene region and pmEGFP-1 plasmid (EGFP).

Generation of Stable Reporter Cell Lines

C2C12 immortalized murine myoblasts cultured in growth media consisting of DMEM (Gibco) with 20% Fetal Bovine Serum (Sigma-Aldrich) at 37° C. with 5% $CO_2$ were transfected with the hSSPN-EGFP or hSSPN-Luciferase linearized plasmids using Lipofectamine 3000 Transfection Reagent (Thermo Fisher Scientific). Transfected cells were selected using 800 μg/ml of G418 (Sigma-Aldrich) for 4 weeks to generate stable cell lines expressing reporter protein under control of the human SSPN promoter.

High-Throughput Screening hSSPN-EGFP myoblasts were seeded at 500 cells per well in 50 μl of growth media in 384-well black, clear bottom microplates (Greiner) using a Multidrop 384 (Thermo Fisher Scientific) and incubated for 3 days. Upon reaching confluency, the growth media was replaced with 50 μl of differentiation media consisting of DMEM with 2% horse serum (Sigma-Aldrich) using an EL406 combination washer dispenser (Biotek). At day 2 of differentiation, the media on the cells was aspirated, left with a residual volume of 10 μl, and replaced with 30 μl of fresh differentiation media. 0.5 μl of small molecule in DMSO or DMSO alone (for vehicle and positive control wells) was added to each well using a Biomek Fx (Beckman). To ensure proper mixing of the DMSO, 50 μl of additional differentiation media was added to all wells except the positive control treated wells, which instead received 50 μl of media containing insulin transferrin selenium (ITS, Gibco) to reach a final concentration of 1% ITS. The final concentration of drug in each treated well was 5.5 μM in 0.55% DMSO and 0.55% DMSO for vehicle and positive control treated wells. After 48 hours of incubation, the media was replaced with Fluorobrite DMEM (Gibco) and each plate was imaged using ImageXpress Micro Confocal High Content Imaging System (Molecular Devices). The fluorescent intensity of imaged cells was determined using MetaXpress Analysis software (Molecular Devices). Analysis setting were as follows: top hat (size: 12, filter shape: circle), adaptive threshold (source: top hat, minimum width: 10, maximum width: 800, intensity above local background: 500), filter mask (filter type: minimum area filter, minimum value: 500).

Luciferase Assay hSSPN-Luciferase myoblasts were cultured as described above. After 48 hours of treatment, plates were allowed to equilibrate to room temperature before the media was aspirated using an EL406 combination washer dispenser at room temperature. Bright-Glo luciferase assay system reagent (Promega) and differentiation media were added to cells at a 1:2 dilution using a Multidrop 384. After a 3-minute incubation at room temperature, luminescence signal was quantified using an Envision plate reader (PerkinElmer). The relative luminescence units were analyzed to determine fold change of treated over vehicle treated cells.

C2C12 and H2K Mdx Cell Culture

C2C12 cells (American Type Culture Collection) were grown at 37° C. with 5% $CO_2$ in growth media containing DMEM (Gibco) with 20% FBS (Sigma-Aldrich). Upon reaching confluency, the media was replaced with differentiation media containing DMEM with 2% horse serum (Sigma-Aldrich). Conditionally immortalized H2K mdx myoblast cells with a nonsense mutation in exon 23 of dystrophin were a gift from Terrance Partridge, Ph.D. (Children's National Medical Center, Washington, D.C.). Cells were allowed to proliferate on 0.01% gelatin (Sigma-Aldrich) coated plates at 33° C. with 5% $CO_2$ with growth media containing DMEM, 20% HI-FBS (Invitrogen), 2% L-glutamine (Sigma-Aldrich), 2% chicken embryo extract (Accurate Chemical), 1% penicillin-streptomycin (Sigma-Aldrich), and 20U/ml of fresh interferon gamma (Gibco). For differentiation, H2K mdx myoblasts were seeded on plates coated with 0.1 mg/ml matrigel (Corning) diluted in DMEM and grown in proliferation conditions. Upon reaching confluency, cells were grown at 37° C. with 5% $CO_2$ in differentiation media containing DMEM with 5% horse serum (Sigma-Aldrich), 2% L-glutamine, and 1% penicillin-streptomycin using established protocols.

In Vitro Treatments

Cells were treated for 48 hours beginning at day 2 of differentiation with DMSO (vehicle control, ATCC), felodipine (Sigma), nilvadipine (Sigma), alloxazine (Sigma), GW5074 (Sigma), methylthioadenosine (Santa Cruz Biotechnology), or ezutromid (Cayman Chemicals) diluted in cell type specific differentiation media at doses listed in the figures. For gene expression studies, each treatment was performed in duplicate. For protein studies, each treatment was performed with single or double replicates.

Immunoblotting

C2C12 murine myotubes treated for 48 hours were lysed using RIPA buffer (Thermo Fisher Scientific) containing a protease inhibitor cocktail (0.6 μg/ml pepstatin A, 0.5 μg/ml aprotinin, 0.5 μg/ml leupeptin, 0.1 mM PMSF, 0.75 mM benzamidine, 5 μM calpain I inhibitor, 5 μM calpeptin). Cell lysates in RIPA buffer were rocked for 1 hour at 4° C. and centrifuged at 1000 RPM for 30 minutes at 4° C. The supernatant was collected, quantified for protein concentration using the DC protein assay (Bio-Rad), and normalized to 2 mg/ml in water and Laemmli sample buffer with a final concentration of 10% glycerol (Sigma-Aldrich), 5% beta-mercaptoethanol (Sigma-Aldrich), 3% sodium dodecyl sulfate (Sigma-Aldrich), and 0.05% bromophenol blue (Sigma-Aldrich). For SDS-PAGE, samples were heated to 95° C. for 2 minutes before loading 40 μg to a 4-12% tris-glycine gel (Novex), run for 2 hours at 100 volts at room temperature, and transferred to a nitrocellulose membrane for 2 hours at 100 volts at 4° C. Ponceau S staining was performed to visualize protein loading. Membranes were blocked with 5% blotto (5% non-fat dried milk) in tris-buffered saline with 0.1% tween-20 (TBST, Sigma-Aldrich) for 1 hour at room temperature and incubated on a rocker overnight at 4° C. with the following primary antibodies and dilutions in 5% blotto: SSPN (sc-393187, 1:200, Santa Cruz Biotechnology), GAPDH (Mab374, 1:10,000, Millipore). Following three 10-minute TBST washes, the membranes were incubated in goat anti-mouse IgG HRP (Ab6789, 1:5000 for SSPN, 1:10,000 for GAPDH, Abcam) diluted in 5% milk for 2 hours at room temperature. The membranes were then washed three times for 10 minutes each with TBST, incubated in SuperSignal West Pico Chemiluminescent Substrate (Thermo Fisher Scientific) for 5 minutes at room temperature on an orbital shaker, and exposed to autoradiography films (Agfa). Autoradiography films were developed using a SRX-101A tabletop processor (Konica Minolta), scanned to a digital file, and analyzed by densitometry of bands using ImageJ version 1.51s. Target protein bands were normalized to loading control GAPDH with vehicle-treated cells serving as the calibrator sample (relative protein levels of vehicle control=1).

Statistics

All data was analyzed on Prism version 7.0 (GraphPad Software) for Mac OS X using the two-tailed Kolmogorov-Smirnov test. Data are reported as mean±SEM. A p-value of <0.05 was considered statistically significant. *$P<0.05$, $P<0.01$, *$P<0.001$, ****$P<0.0001$.

Example 2: Development of Model Systems for Screening

Figure 3:
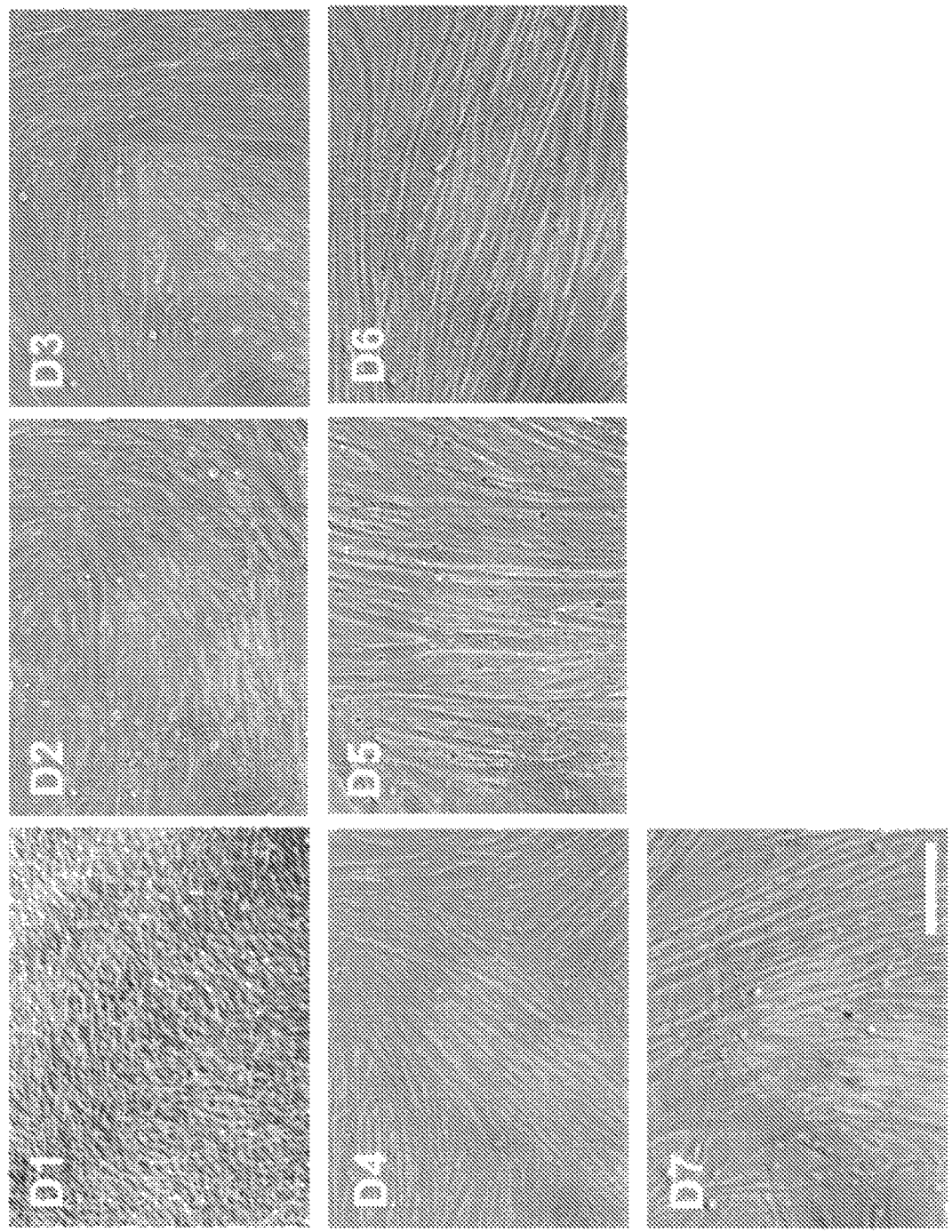
FIG. 3 shows the C2C12 myoblasts undergoing differentiation and fusion into myotubes. Confluent C2C12 myoblasts (day 0, D0) were switched from proliferation to differentiation media and imaged daily using phase contrast microscopy for seven days (D1 to D7). Scale bar=200 μm.

Immortalized C2C12 myoblasts were selected for the screen due to their ease of culture and ability to grow to large quantities. However, it was unclear whether to conduct the assay using immature myoblasts or mature, differentiated myotubes. In order to understand SSPN gene activity in myoblasts and myotubes, SSPN gene expression in C2C12 cells was directly interrogated at each day during differentiation for a total of seven days. Cells underwent fusion starting at day 3 and appeared to be fully differentiated at day 6, as previously reported. SSPN mRNA abundance was relatively unchanged during the first three days following incubation of C2C12 cells in differentiation media (FIG. 1, panel a). However, SSPN levels began to increase exponentially at day 3, reaching ten-fold levels by day 5. The increased SSPN gene expression occurred just after the first evidence of visible myotube fusion at day 3 (FIG. 3).

The expression of SSPN associated proteins was also evaluated, including dystrophin (Dmd), utrophin (Utrn), dystroglycan (Dag), α7 integrin (Itga7), β1D integrin (Itgb1), α-sarcoglycan (Sgca), and β-sarcoglycan (Sgcb).

Figure 4:
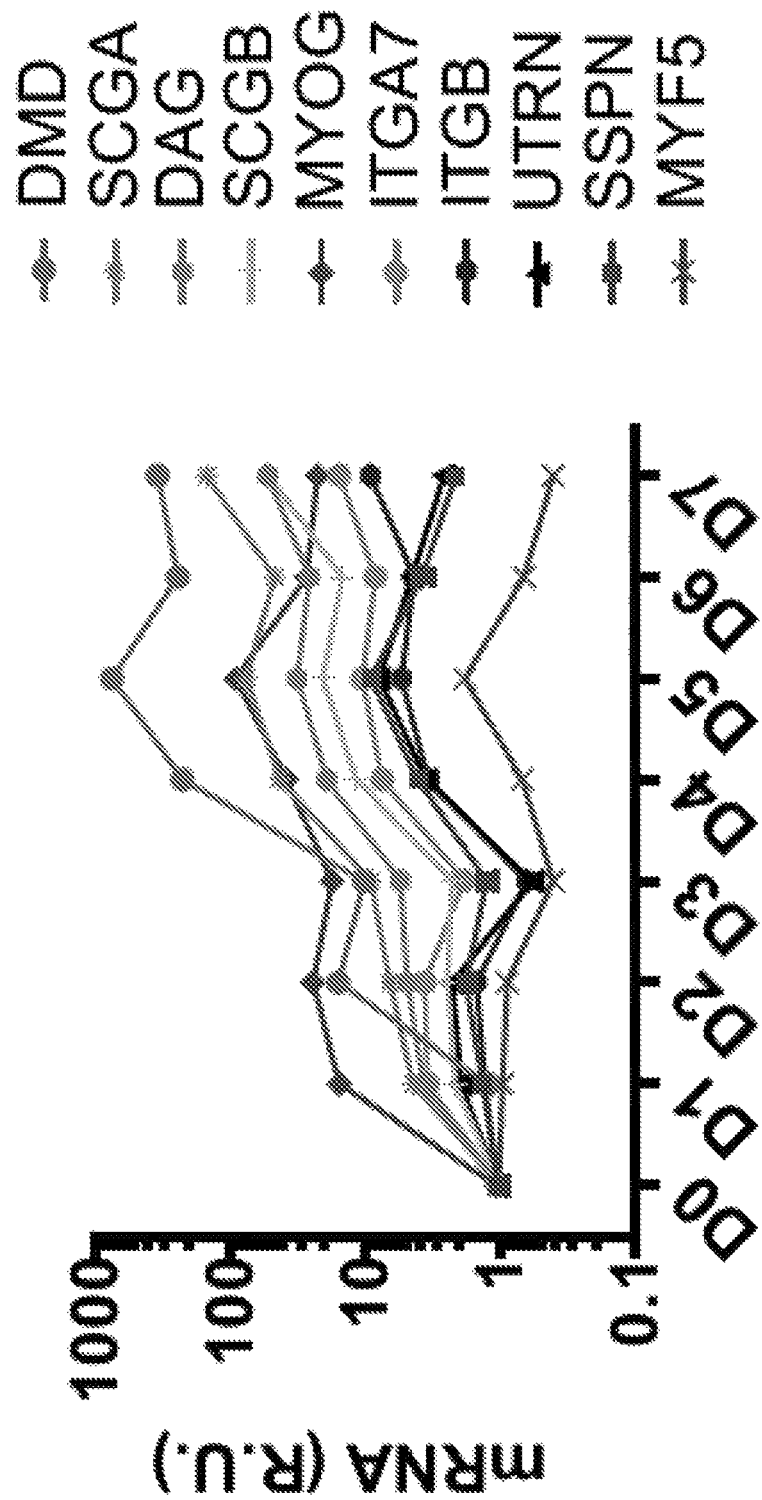
FIG. 4 shows a summary of gene expression of myofiber membrane adhesion complex members during C2C12 differentiation. Expression of individual genes encoding protein components of the three major adhesion complexes (DGC, UGC, and α7β1D-integrin complex) were investigated, including: (a) SSPN, sarcospan; (b) DMD, dystrophin; (c) UTRN, utrophin; (d) DAG, dystroglycan, (e) SCGA, α-sarcoglycan; (f) SCGB, β-sarcoglycan; (g) ITGA7, α7 integrin; (h) ITGB1, (β1D integrin; (i) MYOG, myogenin; and (j) MYF5, myogenic factor 5. Gene expression was calculated using the ddCt method and normalized to β-actin with day 0 (myoblast) values serving as the calibrator sample (n=3). R.U., relative units.

Gene activity increased immediately after myoblasts were switched from proliferation to differentiation media (FIG. 1, panels b-i, and FIG. 4). Interestingly, while dystrophin was not expressed in myoblasts, dystrophin mRNA levels increased nearly 1,000-fold during differentiation. Utrn, Itga, and Itgb 1 expression increased by ten-fold, while the sarcoglycans and dystroglycan increased nearly one hundred-fold during the same time period (FIG. 1). As a control, muscle-specific transcription factors, myogenin (MyoG) and myogenic factor 5 (Myf5), that are known to regulate specific steps during myoblast differentiation were evaluated. MyoG gene activity increased immediately upon exposure to differentiation conditions (FIG. 1, panel i), while Myf5 gradually decreased (FIG. 1, panel j). Based on these results, cells were treated at day 2 of differentiation and data was collected at day 4 of differentiation as this would allow for increases in gene expression while minimizing possible saturation of gene activation.

Figure 2:
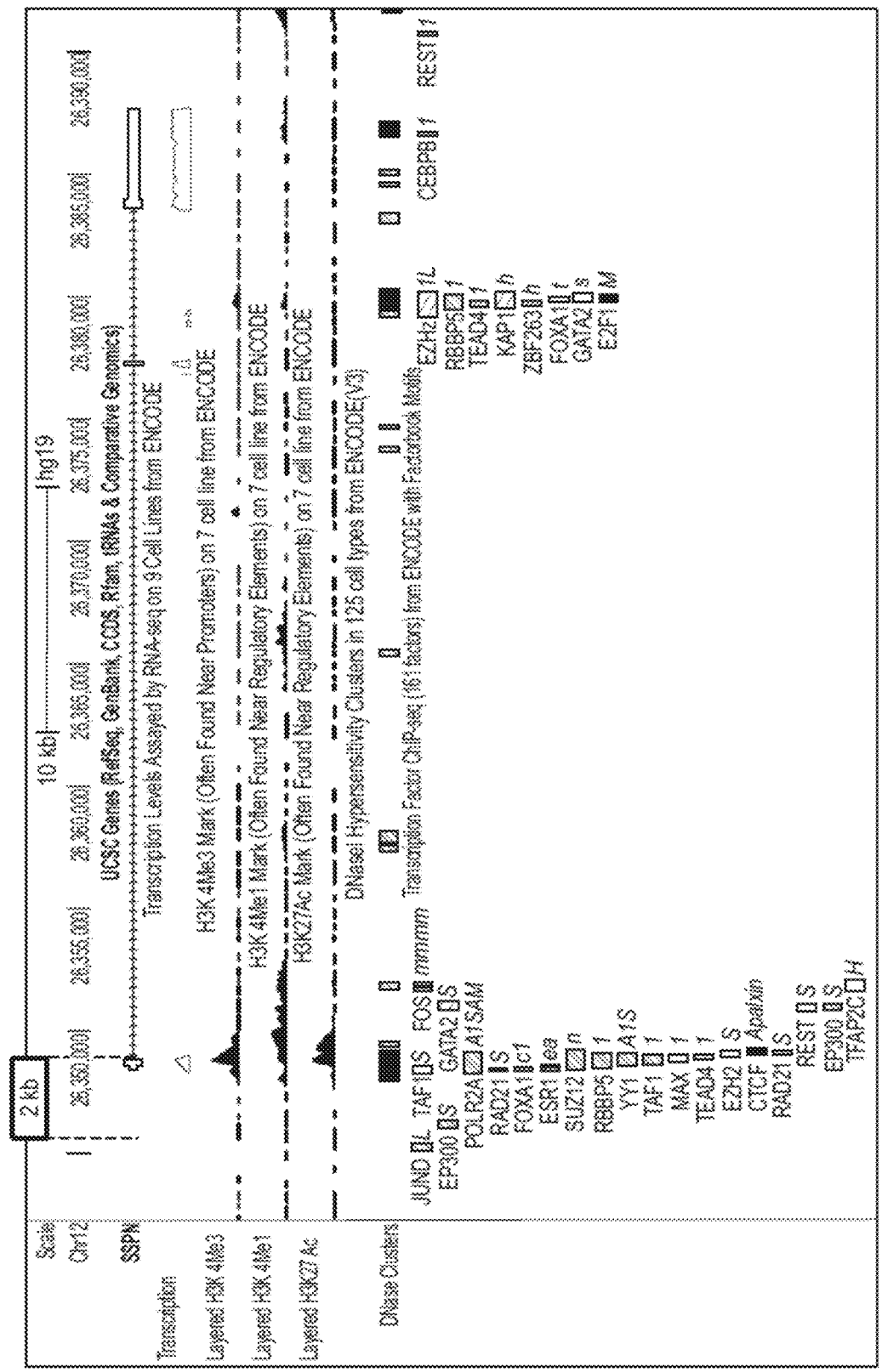
FIG. 2 shows the predicted human SSPN promoter region determined using UCSC genome browser. H2K4me3 marks, DNase hypersensitivity regions, and ChIP-seq data reveal predicted transcription factor binding sites in human skeletal muscle cultures. These analyses indicate that the SSPN promoter includes region upstream of exon 1 and within exon 1. Shown is skeletal muscle and cardiac-specific transcript variant 1 (NM_005086.4) of the human SSPN gene (NG_012011.2) in UCSC Genome browser human February 2009 (GRCh37/hg19) assembly. Location shown: chr12:26,342,405-26,392,014.
Figure 7:
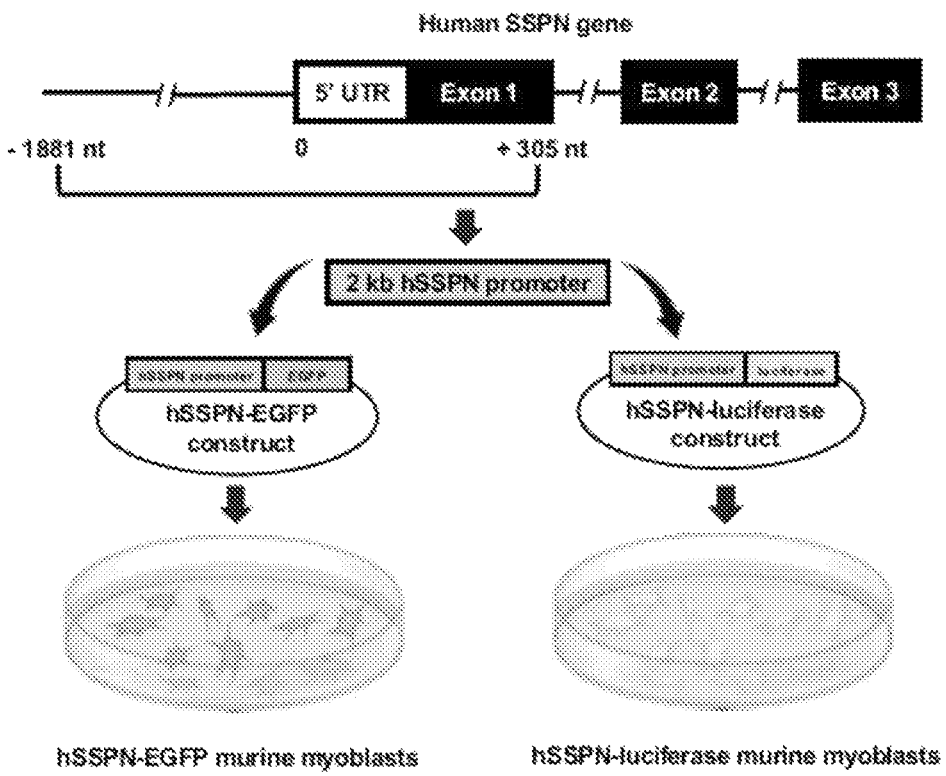
FIG. 7 has four panels, a-d, which show that the generation and validation of biologically relevant myoblasts show effective reporting of sarcospan gene activity. The promoter region of the muscle-specific human sarcospan (hSSPN) gene was predicted using UCSC genome browser gene regulatory data. Using traditional cloning techniques, (a) a 2 kb region of the predicted hSSPN promoter was amplified and inserted into promoterless plasmids containing the EGFP or luciferase gene. These constructs were used to transfect C2C12 murine myoblasts reporter cell lines, which were then selected for stable transfection using antibiotic selection. Confluent hSSPN-EGPF or hSSPN-luciferase reporter myoblasts (day 0, D0) were switched from proliferation to differentiation media and assayed every other day for eight days (D1 to D8). (b) High-content imaging of differentiating hSSPN-EGFP cells showed an increase in EGFP expression over time (n=88 per time point). (c) hSSPN-luciferase cells were subjected to Bright-Glo luminescence assay and also showed an increase in reporter activity as the myoblasts differentiated into myotubes (n=19-47 per time point). (d) High-content imaging of hSSPN-EGFP cells demonstrates a transition to mature myotube morphology that correlates with an increase in reporter signal. Fluorescence and luminescence values are reported as relative fold change over myoblast values (R.U., relative units). Scale bar, 100 μm. ****$p<0.0001$.
Figure 7:
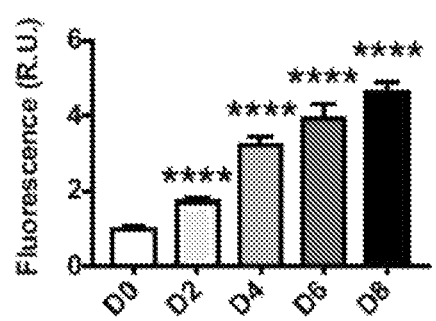
Figure 7:
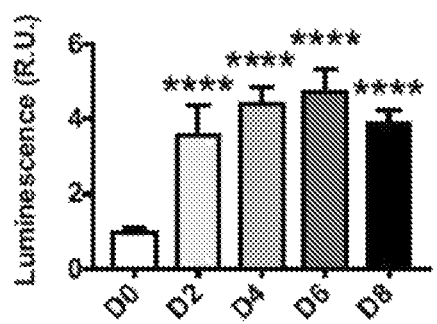
Figure 7:
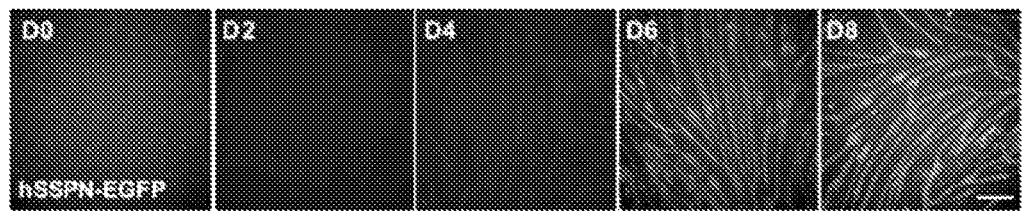

Example 3: Generation and Validation of Biologically Relevant Reporters of SSPN Gene Activity To identify the human SSPN (hSSPN) promoter region, publically available data on UCSC genome browser was used. By assessing H2K4me3 marks, DNase hypersensitivity regions, and ChIP-seq data showing transcription factor binding, the promoter was predicted to be located directly upstream of exon 1 and within exon 1 (FIG. 2). As gene activity can be easily visualized without the need for costly reagents, a fluorescence-based reporter for the primary screening assay was selected. A more reagent-consuming luminescence assay was used as the counterscreen to eliminate false positives from auto-fluorescent compounds. The immortalized C2C12 mouse myoblast cell line was used to generate stably transfected reporter cells containing an enhanced green fluorescent protein (EGFP) or luciferase reporter driven by the human sarcospan promoter (hSSPN) (FIG. 7, panel a). The hSSPN-EGFP and hSSPN-Luciferase myoblasts expressed reporter protein at increasing levels throughout differentiation into early-stage myotubes, revealing that the reporters are reflective of endogenous SSPN gene activity (FIG. 7, panel b). Insulin transferrin selenium (ITS) was selected as a positive control for the screening assays as it increases hSSPN-EGFP and hSSPN-Luciferase reporter levels by 1.4-fold over vehicle after 48 hours of treatment (FIG. 5), showing that the reporter cells are responsive to chemical stimulus. ITS increases protein synthesis and enhances the rate of myotube fusion, which increases SSPN expression as previously shown (FIG. 1, panel a). Cells transfected with reporter plasmids lacking the SSPN promoter did not exhibit fluorescence or luminescence reporter activity.

Example 4: Determining Optimal Assay Conditions for High-Throughput Screening

Figure 8:
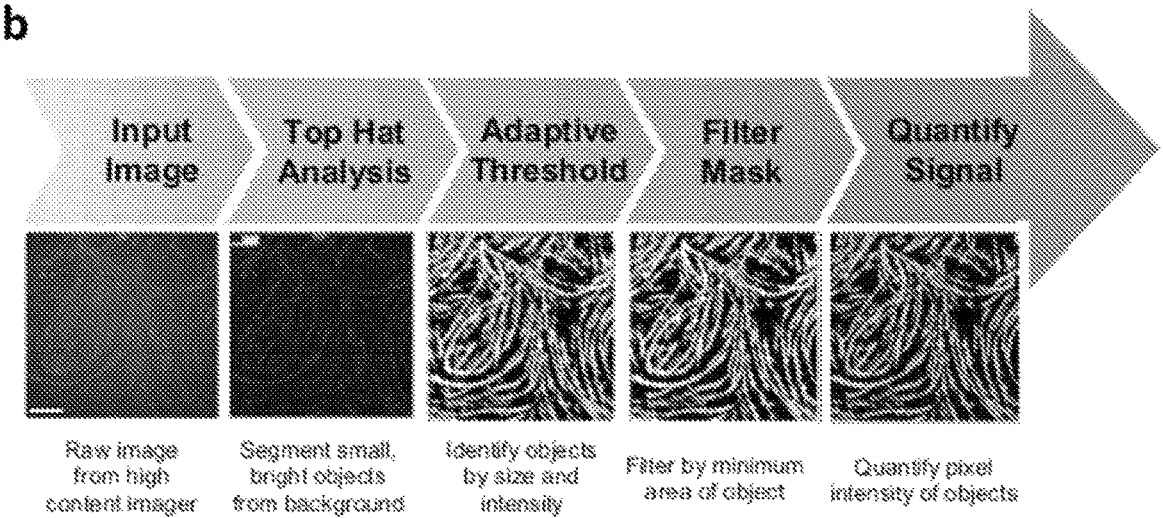
FIG. 8 has three panels, a-c, that show miniaturized cell-based assay used to identify compounds that increase hSSPN-EGFP expression through high-content imaging and analysis. (a) Assay parameters optimized for high-throughput screening of hSSPN-EGFP myotubes. High-throughput assay conditions were optimized for a 384-well microplate format screen on hSSPN-EGFP reporter myotubes treated with a concentrated stock solution of 1 mM small molecule in 100% DMSO. Assay parameters optimized for C2C12 myotube screening were developed in the Molecular Screening Shared Resource facility using specialized, automated equipment (see Methods). (b) High-content image analysis workflow. The MetaXpress custom analysis module processed images from high-content imaging by transforming the input image to remove background (Top Hat Analysis), identifying cells by size and intensity above local background (Adaptive Threshold), excluding debris by minimum area (Filter Mask), and quantifying fluorescence intensity of each resulting image. Scale bar, 220 μm. (c) The custom analysis module generated 384 data points per well and reliably detected significant differences between cells treated with vehicle (left) and positive control, 1% insulin transferrin selenium (right). Shown is representative data from a plate of hSSPN-EGFP cells treated with vehicle, compound, or positive control for 48 hours.

Assay development is a challenging and laborious process that requires iterations of optimization. The obstacles that arise during assay development are confounded by the need to miniaturize assays and minimize the number of steps required, which both decrease handling time and directly increase throughput. To effectively screen large compound libraries, assays were scaled down to a 384-well microplate format, which allowed for reduced reagent consumption and quick data collection. To optimize assay conditions for high-throughput screening in a 384-well microplate format, numerous parameters for both hSSPN-EGFP and hSSPN-Luciferase reporter C2C12 cells were evaluated (FIG. 8, panel a).

One limiting factor in high-throughput screens is the preparation of large quantities of cells. Subsequently, multiple seeding densities ranging from 500 to 4000 cells per well were assessed. Seeding 500 cells per well followed by 3 days of incubation was sufficient for the myoblasts to reach confluency before differentiation. This also reduced the amount of pre-screen culture required, making it an optimal condition for scaling up to meet high-throughput requirements.

Figure 5:
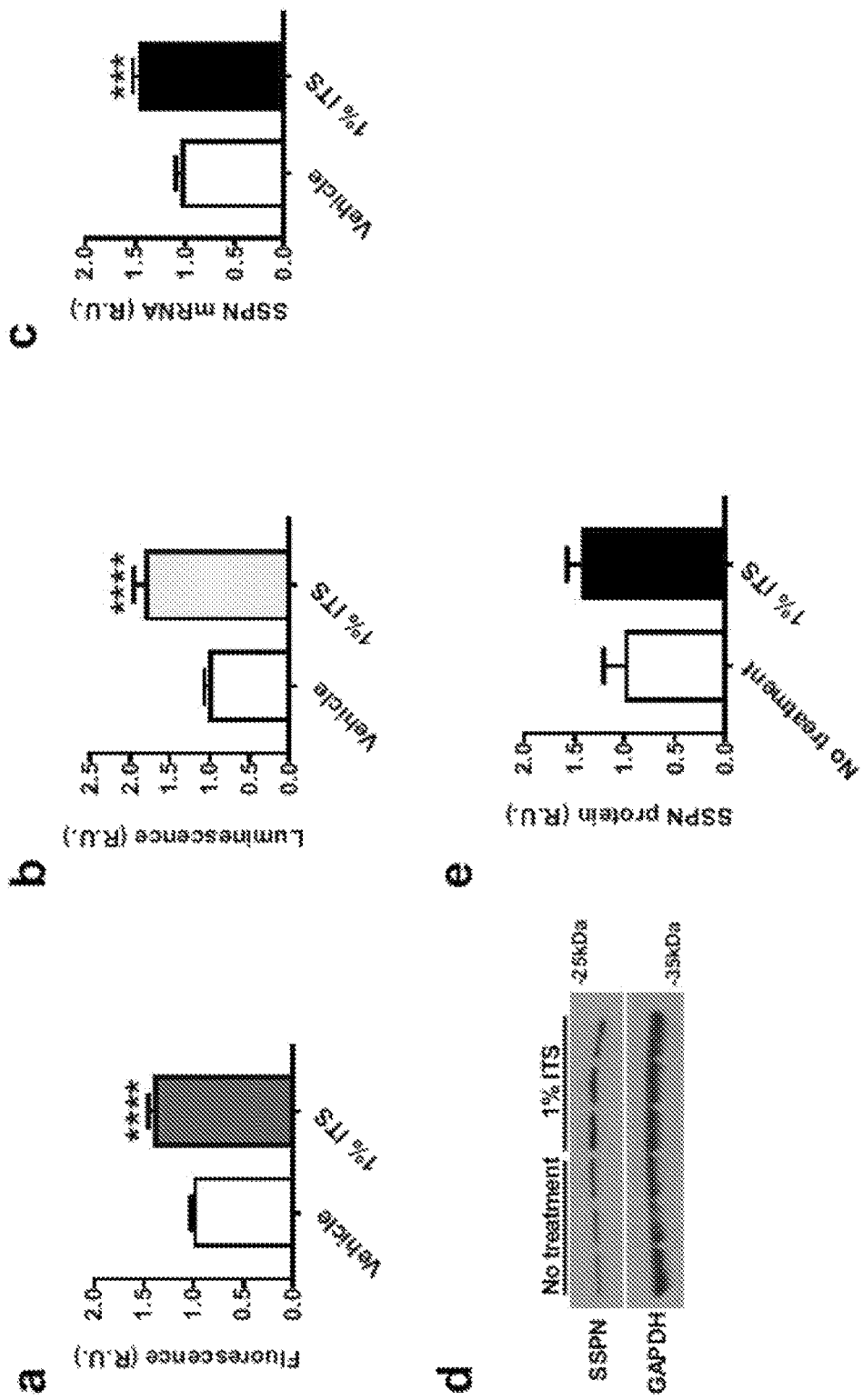
FIG. 5 has five panels, a-e, which show that the sarcospan reporter, gene, and protein levels increase similarly after treatment with positive control. Treatment with 1% insulin transferrin selenium (ITS) increased (a-b) hSSPN-EGFP and hSSPN-luciferase reporter levels (n=10-21), (c) SSPN transcript (n=3) and (d-e) SSPN protein levels (n=3) in wild-type C2C12 myotubes after 48 hours of treatment. Images of the hSSPN-EGFP cells were analyzed using a MetaXpress custom analysis module. For immunoblot analysis, total cell lysate was probed with anti-SSPN antibody. GAPDH is shown as a loading control. Quantification for immunoblot shown in panel (d). All cells were treated at day 2 of differentiation and assayed at day 4 of differentiation. Data reported as fold-change over vehicle-treated cells. *$p<0.001$, **$p<0.0001$.
Figure 6:
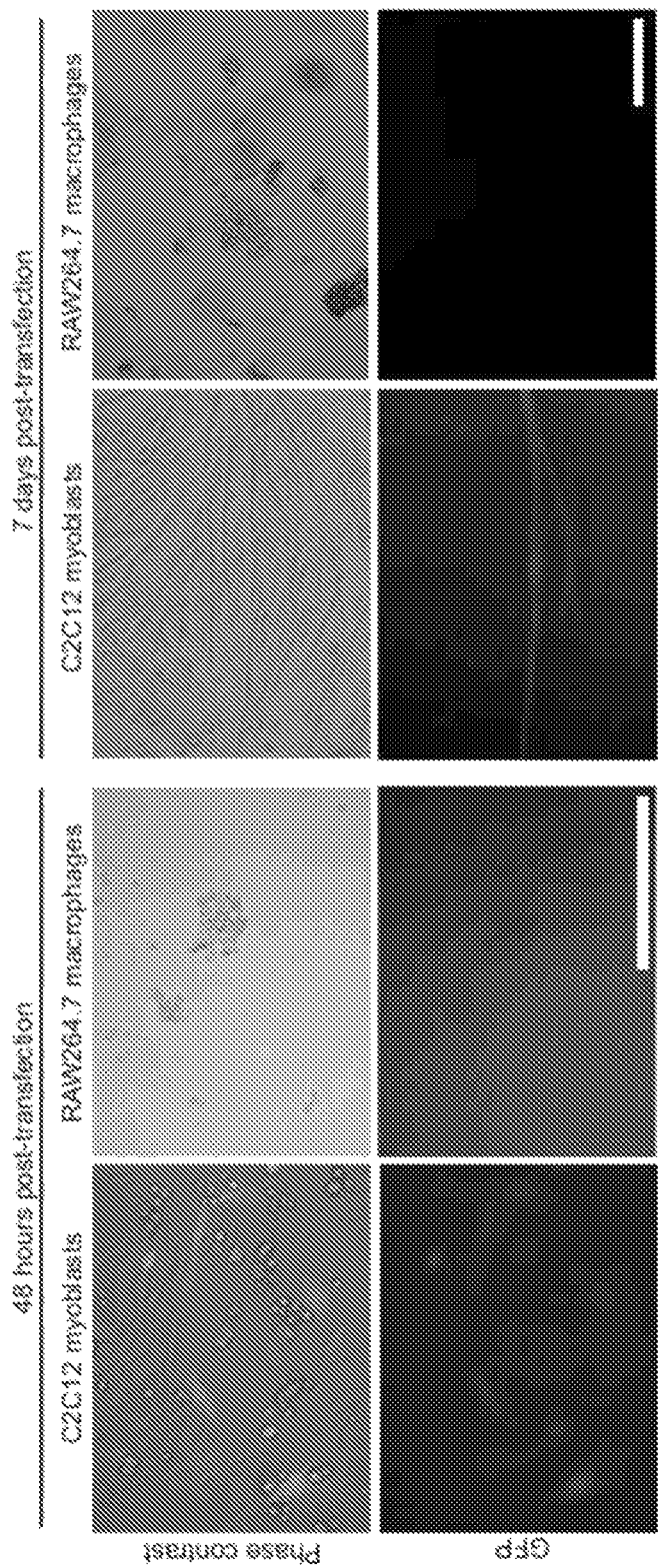
FIG. 6 shows that the hSSPN-EGFP construct is expressed in a cell-type specific manner. The hSSPN-EGFP plasmid was transfected in C2C12 murine myoblasts or RAW264.7 murine macrophages. At 48 hours and 7 days post-transfection EGFP was detected in the myoblasts, but not the macrophages. Scale bar=100 μm.

Next, the ability of the ITS positive control to increase reporter activity after 24 and 48 hours was tested. A detectable and significant change in reporter activity after 48 hours of treatment was observed (FIG. 5). Screening core facilities typically store small molecules in 100% DMSO, which can lead to cell toxicity from the DMSO vehicle alone. To assess DMSO toxicity in our cells, cells were dosed with 0.1-10% DMSO. A decrease in cell viability at 2% DMSO and higher after 48 hrs of treatment was observed. To ensure proper DMSO mixing to prevent regionally high concentrations of DMSO that can negatively impact cell viability, several mixing methods and conditions were tested. From these tests, it was determined that the addition of 0.5 µl of 100% DMSO to an initial volume of 40 µl of media in each well, followed by 50 µl of additional media was sufficient to create a homogenous solution of DMSO, as detected by DMSO spiked with crystal violet dye. Image analysis using a custom analysis module in MetaXpress software identified myotubes based on specified dimensions and quantifies fluorescence pixel intensity of identified cells (FIG. 8, panel b). Imaging two regions of each well at 10× magnification in low fluorescence media was sufficient for the custom analysis module to reliably detect a significant difference between vehicle and positive control treated cells (FIG. 8, panel c).

Example 5: High-Throughput Screening on hSSPN-EGFP Myotubes

Figure 9:
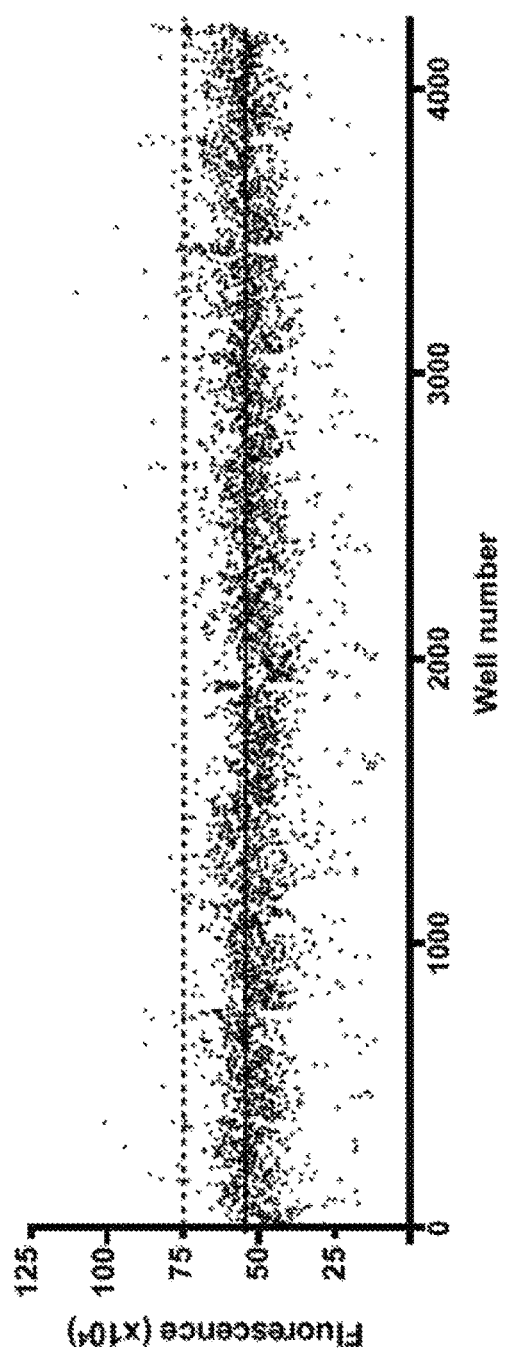
FIG. 9 has two panels, a-b, among which (a) shows high-throughput screening of LOPAC, NIH, and Prestwick libraries on hSSPN-EGFP myotubes, and (b) shows hits from high-throughput screening of hSSPN-EGFP myotubes. (a) hSSPN-EGFP cells differentiated for two days were used to screen 3,200 molecules in the Library of Pharmacologically Active Compounds, NIHII, and Prestwick libraries (n=1). The reporter cells were treated with 5.5 μM of compound and imaged 48 hours later at day 4 of differentiation into myotubes. Two images per well were captured and analyzed using a MetaXpress custom analysis module to quantify fluorescence intensity. The solid line marking the average fluorescence of all data points and the dashed line marking the cut-off for hits (1.4-fold over vehicle). (b) The screen of 3,200 compounds resulted in 13 hits, which included an overrepresented number of L-type calcium channel blockers (felodipine, isradipine, lacidipine, nifedipine, and nilvadipine) and one hit (felodipine) which appeared as a hit twice from two independent libraries. Robust strictly standardized mean difference (SSMD*) was used to classify the strength of each hit. SSMD*>0.25 and 1.4-fold change over vehicle was the minimum to be considered a hit. R.U., relative units.

To gain insight into the pathways involved in SSPN upregulation, libraries of well-characterized FDA approved compounds were screened. Using the hSSPN-EGFP cells, the Library of Pharmacologically Active Compounds (LOPAC), Prestwick Chemical, and NIHII small molecule libraries totaling 3,200 small molecules was screened. All images were analyzed for cellular fluorescence intensity and compared with values from vehicle treated cells. A hit cutoff of 1.4-fold fluorescence intensity over vehicle was set and images with debris or small molecules that auto-fluoresce were eliminated. This led to 13 small molecules (FIG. 9, panel b). Among the thirteen hits, six are L-type calcium channel antagonists (felodipine, isradipine, lacidipine, nifedipine, nilvadipine) with felodipine appearing twice from the LOPAC and NPW libraries, which indicated the robustness of the assay in duplicating results. In addition, at least five additional hits (isoproterenol, aceclidine, alloxazine, GW5074, and nandrolone) also affected intracellular calcium levels (an earlier assay also included AC-93253 and methylthioadenosine among the hits). These data strongly supported that endogenous SSPN expression is regulated in a calcium-dependent manner.

Table 3 provides information on plate quality control using robust strictly standardized mean difference. Robust strictly standardized mean difference (SSMD*) was used a measurement of quality control. Each of the 11 plates resulted in an SSMD*>1, indicating a good quality difference between vehicle and positive control-treated cells.

TABLE 3

| Plate | Library | SSMD* |
|---|---|---|
| 1 | LOPAC1 | 1.0 |
| 2 | LOPAC2 | 1.7 |
| 3 | LOPAC3 | 1.1 |
| 4 | LOPAC4 | 1.0 |
| 5 | NPW1 | 1.6 |
| 6 | NPW2 | 1.6 |
| 7 | NPW3 | 1.0 |
| 8 | NPW4 | 1.4 |
| 9 | NIHII1 | 1.8 |
| 10 | NIHII2 | 1.0 |
| 11 | NIHII3 | 1.1 |

Table 4 shows that validated hits from hSSPN-EGFP screen reveal an enrichment of calcium channel blockers. The screen resulted in 13 hits, which were further validated with the hSSPN-EGFP reporter cells. The validated hits included an overrepresented number of L-type calcium channel blockers.

TABLE 4

| Compound | Description |
|---|---|
| Felodipine | L-type $Ca^{2+}$ channel blocker |
| GW5074 | cRaf1 kinase inhibitor |
| Isoproterenol | Sympathomimetic amine acting on β-adrenoceptors |
| Isradipine | L-type $Ca^{2+}$ channel blocker |
| Lacidipine | L-type $Ca^{2+}$ channel blocker |
| Nandrolone | anabolic-androgenic steroid |
| Nilvadipine | L-type $Ca^{2+}$ channel blocker |

Table 5 shows the validation of hits from screen on hSSPN-EGFP myotubes. Hits from the screen were retested on hSSPN-EGFP myotubes at 5.5 µM in 2 plates (n=24 per plate). RFU, relative fluorescence units. *SSMD, robust strictly standardized mean difference.

TABLE 5

| | hSSPN-EGFP | | | |
|---|---|---|---|---|
| | Plate 1 | | Plate 2 | |
| Compound | RFU | SSMD* | RFU | SSMD* |
| Aceclidine | 1.1 | −0.07 | 1.1 | 0.25 |
| Acyclovir | 0.9 | −0.37 | 1.0 | 0.19 |
| Alloxazine | 1.0 | −0.03 | 1.1 | 0.21 |
| Carbodox | 1.1 | 0.21 | 1.1 | 0.43 |
| Felodipine | 1.4 | 1.75 | 1.4 | 1.56 |
| GW5074 | 1.2 | 0.67 | 1.2 | 0.78 |
| Isoproterenol | 1.1 | 0.26 | 1.1 | 0.26 |
| Isradipine | 1.5 | 1.79 | 1.4 | 1.50 |
| Lacidipine | 1.3 | 0.69 | 1.2 | 1.02 |
| Nafadotride | 1.1 | −0.09 | 1.0 | −0.01 |
| Nandrolone | 1.2 | 0.44 | 1.1 | 0.41 |
| Nifedipine | 1.3 | 0.41 | 1.0 | 0.22 |
| Nilvadipine | 1.6 | 1.08 | 1.5 | 0.97 |

Figure 10:
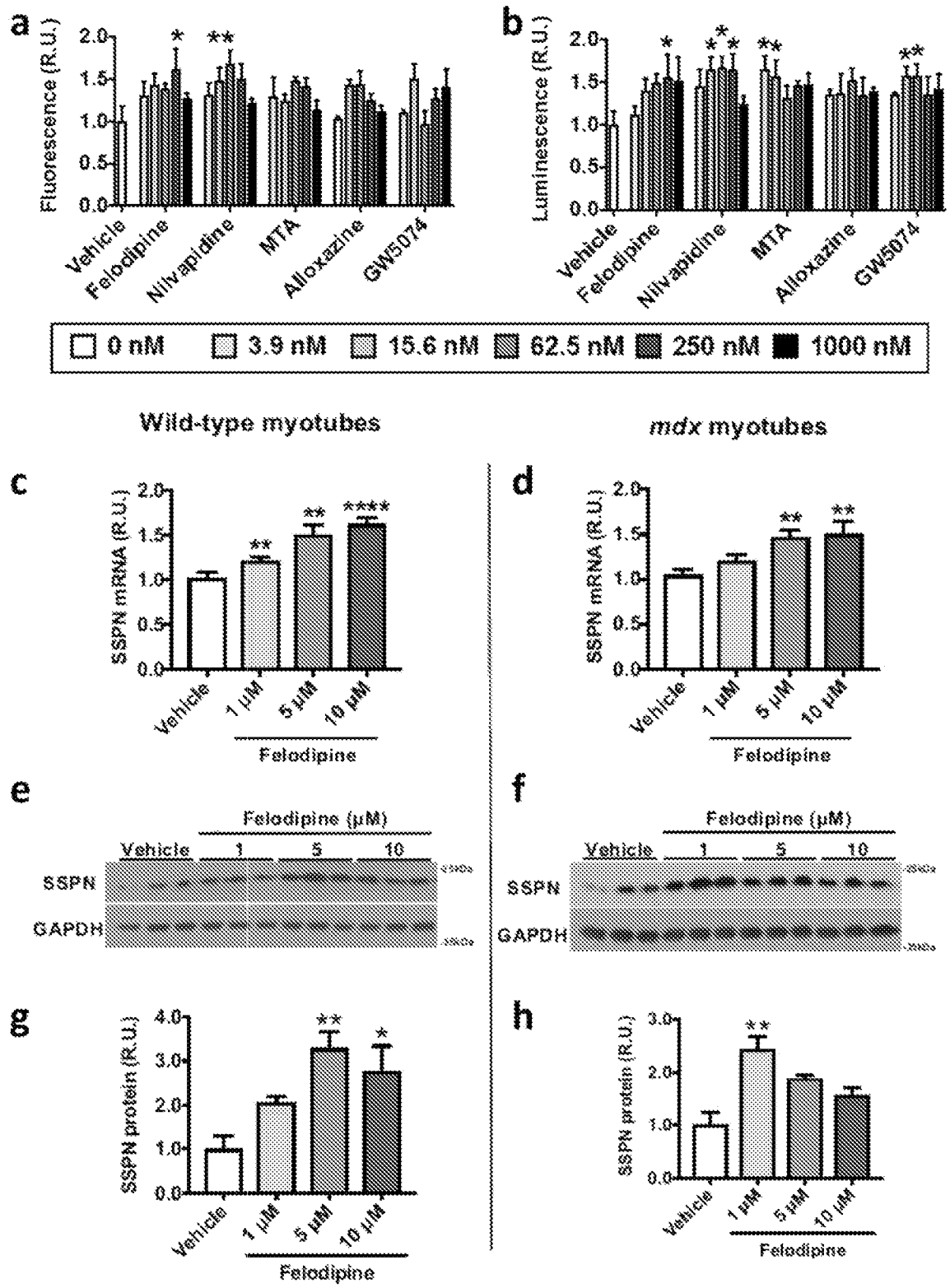
FIG. 10 has eight panels, a-h, which show that a compound identified in high-throughput screen increases sarcospan transcript and protein levels in both wild-type and dystrophin-deficient mdx myotubes. (a-b) hSSPN-EGFP and hSSPN-Luciferase cells differentiated for two days were treated with a select number of compounds identified in the screen. The cells were treated with doses ranging from 3.9 nm to 1 μM (n=5 each cell line) and assayed 48 hours later. (a) The hSSPN-EGFP and (b) hSSPN-Luciferase cells were responsive to hits identified in the screen. (c-h) Felodipine increases sarcospan gene expression in (c) C2C12 wild-type and (d) mdx myotubes (n=3-8) after 48 hours of treatment. Gene expression was calculated using the ddCt method and normalized to β-actin with vehicle-treated cells serving as the calibrator sample. Using immunoblot analysis, total cell lysate from cells treated with felodipine was probed with anti-SSPN antibodies. GAPDH is shown as a loading control. Felodipine increases sarcospan protein levels in both (e) C2C12 wild-type and (f) and mdx myotubes (n=3). (g-h) Quantification of SSPN protein levels are normalized to GAPDH. R.U., relative units. All data was obtained from murine myotubes treated for 48 hours and assayed or harvested at day 4 of differentiation. MTA=methylthioadenosine. $*p<0.05$, $p<0.01$, $**p<0.0001$.

Example 6: Counterscreen and Validation of Candidate Drugs in Dystrophin-Deficient Cell Models To validate the primary screen results, a select number of candidate drugs were counterscreened in both hSSPN-EGFP and hSSPN-Luciferase reporter cells in triplicate. The hSSPN-Luciferase cell line was used to exclude molecules that were detected based solely on auto-fluorescence. Felodipine, nilvadipine, methylthioadenosine (MTA), alloxazine, and GW5074 increased activity of both reporters at doses between 3.9 nm to 1 µM after 48 hours of treatment (FIG. 10, panels a-b). To determine whether this increase in human SSPN promoter activity translated to an increase in mouse SSPN transcript levels, C2C12 myotubes were treated with 1-10 µM of felodipine and gene expression was assessed using qPCR. After 48 hours of felodipine treatment, SSPN expression increased over vehicle (FIG. 10, panel c).

To assess the effect of felodipine in a dystrophin-deficient cell model, immortalized mdx myoblasts containing a nonsense mutation in exon 23 of the dystrophin gene were used. Mdx myotubes were treated with 1-10 µM of felodipine. An increase in SSPN gene expression with treatment was observed (FIG. 10, panel d). Because increases in transcript levels do not necessarily correlate with changes in protein levels, SSPN protein levels were also assessed. Immunoblot analysis on C2C12 cells treated with 1 µM-10 µM of felodipine revealed an increase in SSPN protein levels with treatments (FIG. 10, panel e). In mdx cells, treatment with felodipine increased SSPN protein levels (FIG. 10, panel f).

Figure 11:
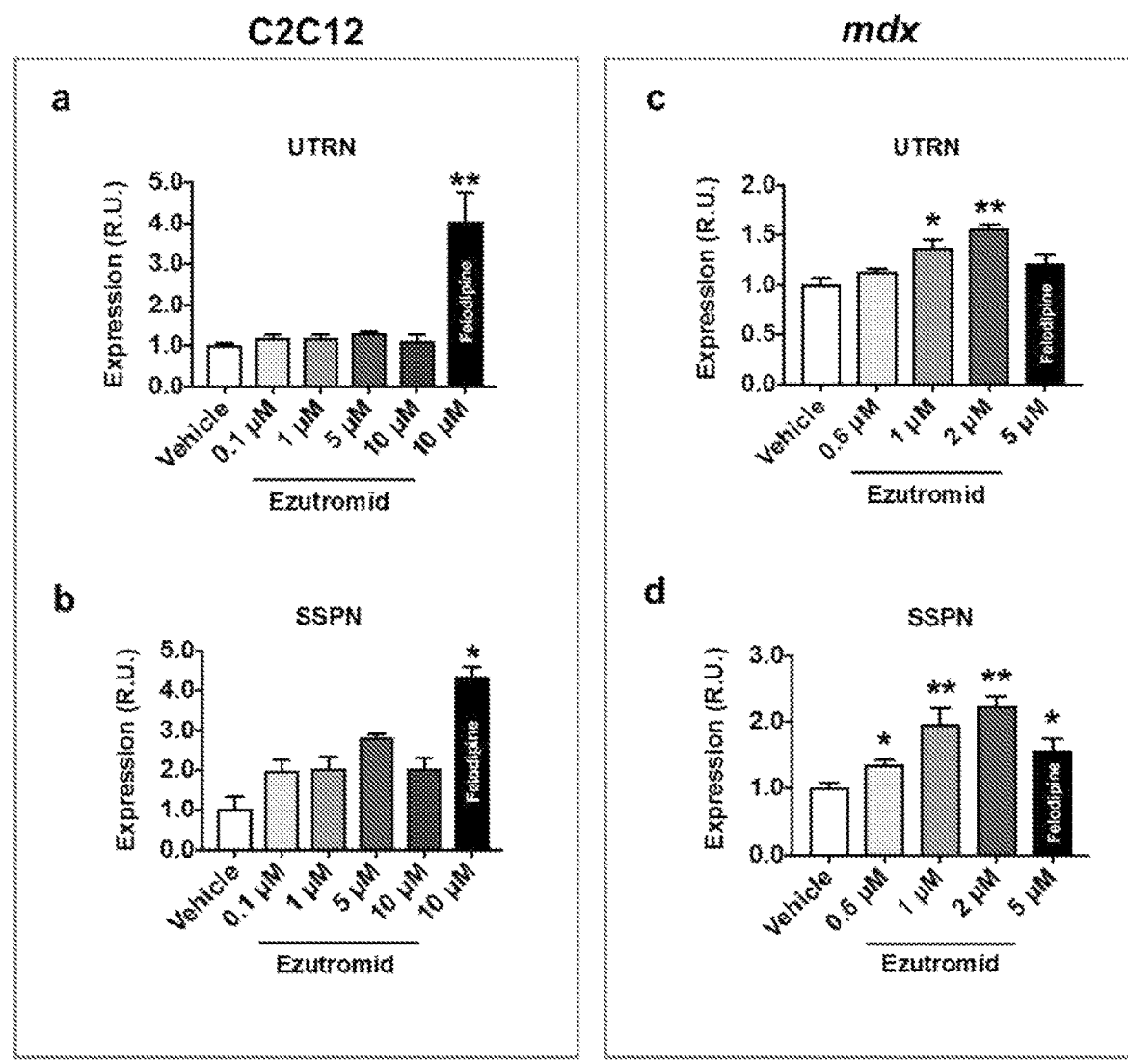
FIG. 11 has four panels, a-d, which show ezutromid and felodipine have different effects on utrophin and sarcospan gene expression in wild-type and dystrophin-deficient myotubes. Utrophin upregulator ezutromid did not increase utrophin gene expression in (a) wild-type (C2C12) myotubes in contrast to felodipine, which increased utrophin levels by four-fold. (b) Ezutromid did not significantly increase sarcospan levels in C2C12 myotubes, while felodipine increased SSPN levels to four-fold over vehicle-treated cells. In dystrophin-deficient (mdx) myotubes ezutromid increased (c) utrophin and (d) sarcospan gene expression levels, while felodipine only increased sarcospan levels. All data were obtained from murine myotubes treated for 48h and harvested at day 4 of differentiation (n=2). Gene expression was calculated using the ddCt method and normalized to GAPDH. Data are expressed relative to vehicle control (R.U., relative units). $*p<0.05$, $**p<0.01$.
Figure 12:
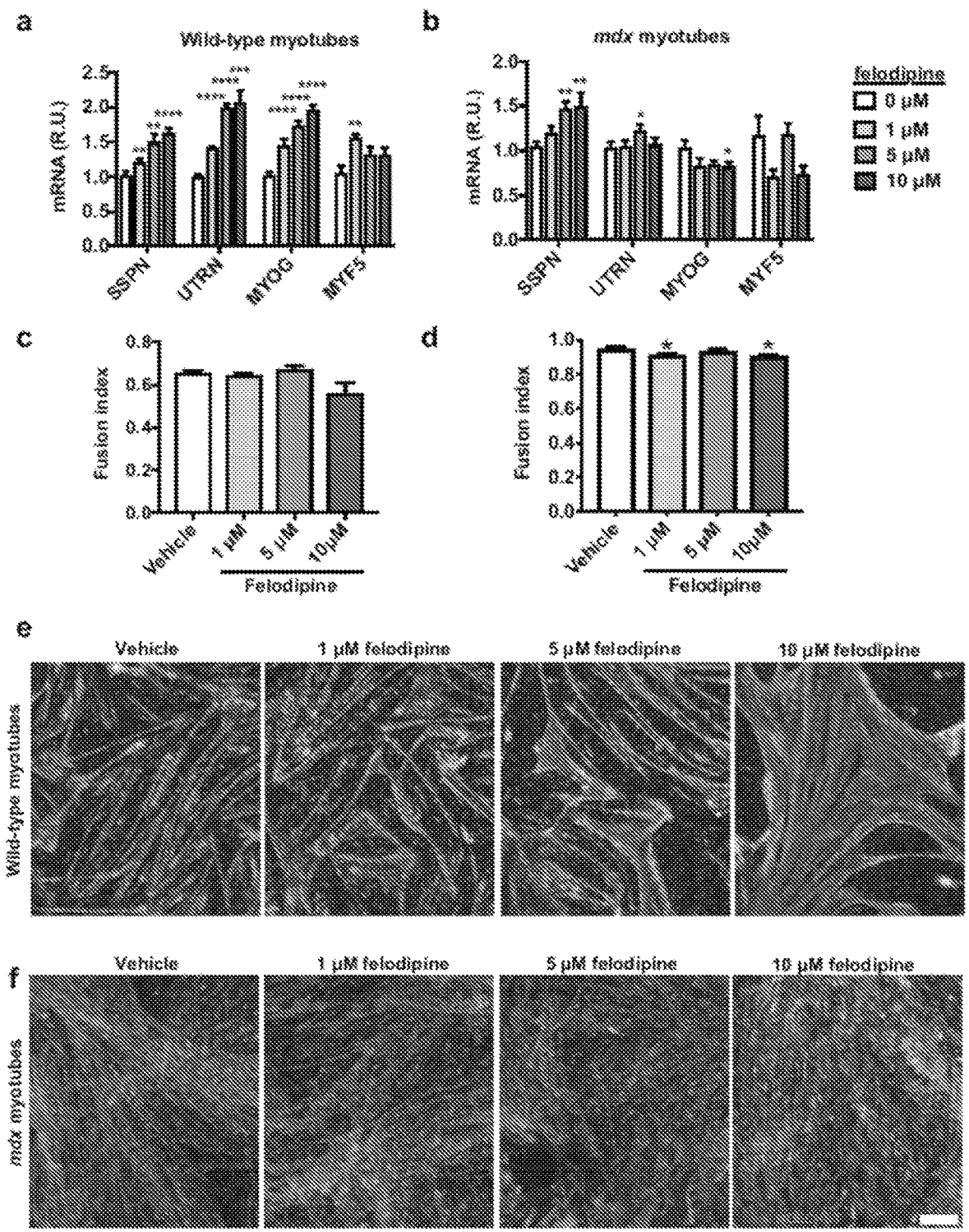
FIG. 12 has six panels, a-f, which show that felodipine enhances differentiation in wild-type, but not dystrophin-deficient myotubes. Felodipine increases utrophin and myogenin gene expression in (a) C2C12 wild-type myotubes, but not (b) mdx myotubes (n=3-8) after 48 hours of treatment (sarcospan gene expression data from FIG. 10). (c-d) Felodipine does not increase fusion index (nuclei in myosin heavy chain positive area/total nuclei in field) in wild-type or mdx myotubes, (e-f) but does induce the formation of hypertrophic wild-type myotubes. Gene expression was calculated using the ddCt method and normalized to β-actin with vehicle-treated cells serving as the calibrator sample. UTRN, utrophin; MYOG, myogenin; MYF5, myogenic factor 5; MHC, myosin heavy chain.
Figure 13:
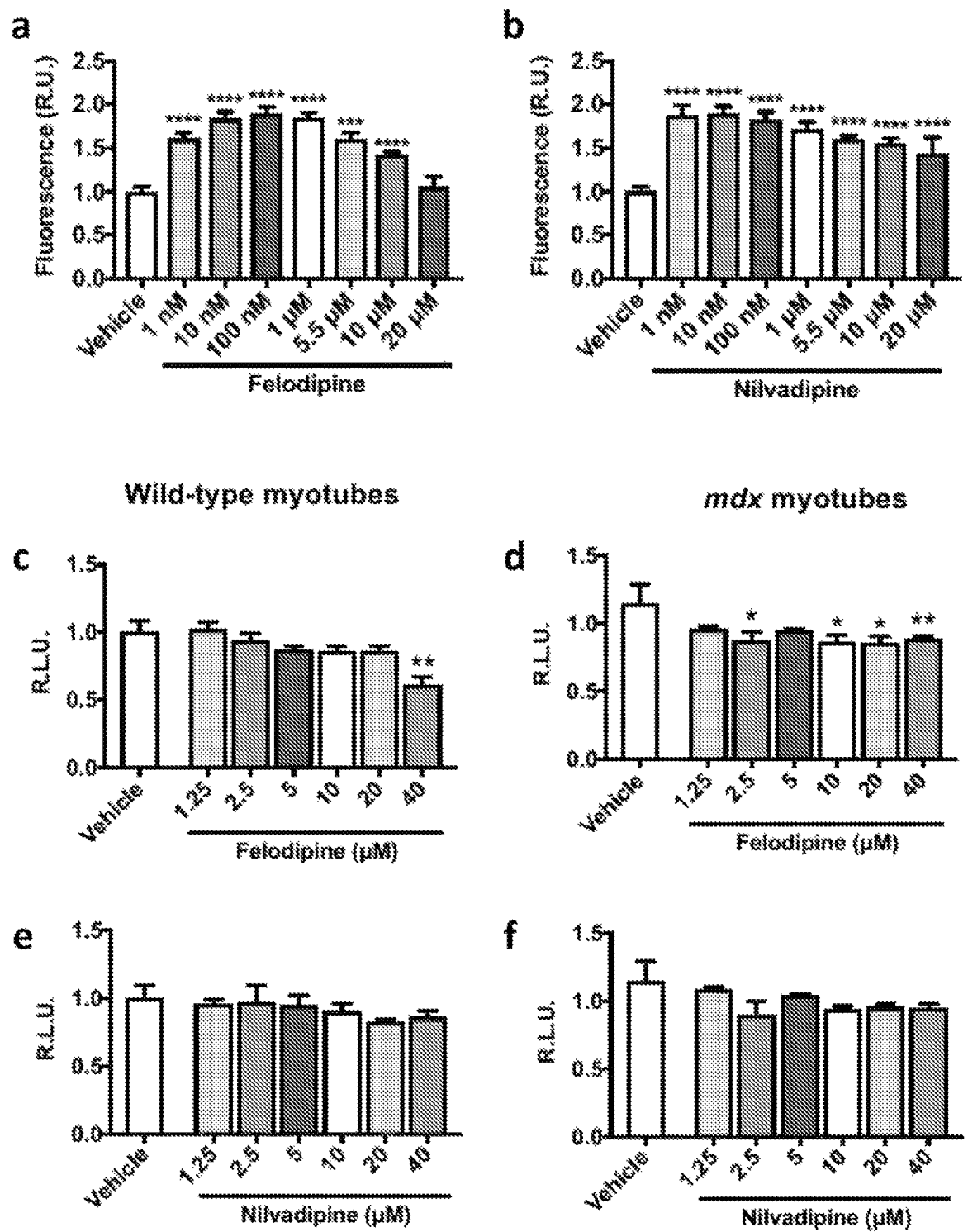
FIG. 13 has six panels, a-f, among which a-b show the titration of screen hits on hSSPN-EGFP myotubes, and c-f show the effect of screen hits on wild-type and mdx cell viability. (a-b) hSSPN-EGFP myotubes were treated with 1 nM-20 μM of felodipine or nilvadipine for 48 hours and imaged using a high-content imager (n=12). Images were analyzed using a MetaXpress custom module to calculate fluorescence over vehicle (R.U., relative units). (c-f) Wild-type and mdx myotubes were treated with 1.25-4 μM of felodipine and nilvadipine and assayed 48 hours later using an ATP-based cell viability assay. (R.L.U., relative luminescence units).

Example 7: Comparison of SSPN Enhancers with Utrophin Upregulators in Clinical Development To assess the effect of SSPN-modulating candidate drugs identified in the screen on gene expression relative to drugs in clinical stage development targeting similar mechanisms, C2C12 cells were dosed with the known UTRN upregulator, ezutromid (SMT C1100). Ezutromid was identified in a similar cell-based, promoter-reporter screen and is currently in clinical trials. While ezutromid did not significantly increase UTRN levels in C2C12 myotubes, a nearly 4-fold increase in UTRN gene expression was observed with 10 µM of felodipine treatment (FIG. 11, panel a). Ezutromid did not significantly increase SSPN gene expression, while treatment with 10 µM of felodipine induced a 4-fold increase in SSPN levels (FIG. 11, panel b). To determine whether ezutromid affected SSPN gene expression in the dystrophin-deficient context, mdx myotubes were treated with ezutromid and UTRN and SSPN transcript levels were quantified. As expected from previously published findings, UTRN expression increased by up to 1.5-fold (FIG. 11, panel c). Interestingly, ezutromid treatment increased SSPN expression by 2-fold, indicating that ezutromid may directly or indirectly increase SSPN levels (FIG. 11, panel d).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for treating or preventing a disease related to dysfunction of a dystrophin-related complex in a subject in need thereof, comprising administering to the subject a compound that increases the expression of sarcospan, wherein the compound is selected from: 2-[3-(1,3-Dihydro-1,3,3-trimethyl-2H-indol-2-ylidene)-1-propenyl]-3-ethyl-benzothiazolium iodide (AC-93253), 1-Azabicyclo[2.2.2]oct-3-yl acetate (aceclidine), 1H-benzo[g]pteridine-2,4-dione (alloxazine), methyl N-[(E)-(1-hydroxy-4-oxidoquinoxalin-4-ium-2-ylidene)methyl]iminocarbamate (carbadox), 4-[1-hydroxy-2-(propan-2-ylamino)ethyl]benzene-1,2-diol (isoproterenol), N-[(1-butylpyrrolidin-2-yl)methyl]-4-cyano-1-methoxynaphthalene-2-carboxamide (nafadotride), or a pharmaceutically acceptable salt or ester thereof.

2. The method of claim 1, wherein the disease related to dysfunction of a dystrophin-related complex is a muscular dystrophy.

3. The method of claim 2, wherein the muscular dystrophy is Becker muscular dystrophy (BMD), congenital muscular dystrophy (CMD), Duchenne muscular dystrophy (DMD), distal muscular dystrophy, Emery-Dreifuss muscular dystrophy, facioscapulohumeral muscular dystrophy, limb-girdle muscular dystrophy, myotonic dystrophy, or oculopharyngeal muscular dystrophy.

4. The method of claim 2, wherein the muscular dystrophy is Duchenne muscular dystrophy (DMD).

5. The method of claim 1, whereby sarcospan mRNA transcript is increased.

6. The method of claim 1, whereby sarcospan protein level is increased.

7. The method of claim 1, wherein the subject is human.

* * * * *

SEQUENCE LISTING

<160> NUMBER OF SEQ ID NOS: 36

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: UTRN F

<400> SEQUENCE: 1
gtatggggac cttgaagcca g                                              21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: UTRN R

<400> SEQUENCE: 2
atcgagcgtt tatccatttg gt                                             22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: DMD F

<400> SEQUENCE: 3
ggaaagcaac acatagacaa cct                                            23

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: DMD R

<400> SEQUENCE: 4
gggcatgaac tcttgtagat cc                                             22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: ITGA7 F

<400> SEQUENCE: 5
gatcgtccga gccaacatca ca                                             22

<210> SEQ ID NO 6

```
<211> LENGTH: 20
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: ITGA7 R

<400> SEQUENCE: 6
ctaacagccc agccagcact                                                  20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: ITGB1 F

<400> SEQUENCE: 7
atgccaaatc ttgcggagaa t                                                21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: ITGB1 R

<400> SEQUENCE: 8
tttgctgcga ttggtgacat t                                                21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: DAG1 F

<400> SEQUENCE: 9
cagacggtac ggctgttgtc                                                  20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: DAG1 R

<400> SEQUENCE: 10
agtgtagcca agacggtaag g                                                21

<210> SEQ ID NO 11
<211> LENGTH: 22
<212> TYPE: DNA
<213> ORGANISM: Artificial Sequence
<220> FEATURE:
```

<223> OTHER INFORMATION: Description of Artificial Sequence: Synthetic
      olignonucleotide
<220> FEATURE:
<223> OTHER INFORMATION: SGCA F

<400> SEQUENCE: 11
gcagcagtaa cttggatacc tc                                              22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: SGCA R

<400> SEQUENCE: 12
aaaggatgca caaacacacg a                                               21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: SGCB F

<400> SEQUENCE: 13
agcacaacag caatttcaaa gc                                              22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: SGCB R

<400> SEQUENCE: 14
aggaggacga tcacgcagat                                                 20

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: SSPN F

<400> SEQUENCE: 15
tgctagtcag agatactccg ttc                                             23

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: SSPN R

```
<400> SEQUENCE: 16
gtcctctcgt caacttggta tg                                              22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: MYOG F

<400> SEQUENCE: 17
gagatcctgc gcagcgccat                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: MYOG R

<400> SEQUENCE: 18
ccccgcctct gtagcggaga                                                 20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: MYF5 F

<400> SEQUENCE: 19
aaggctcctg tatcccctca c                                               21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: MYF5 R

<400> SEQUENCE: 20
tgaccttctt caggcgtcta c                                               21

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: ACTB F

<400> SEQUENCE: 21
tcctgaccct gaagtacccc at                                              22
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: ACTB R

<400> SEQUENCE: 22
ctcggtgagc agcacagggt                                                   20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: GAPDH F

<400> SEQUENCE: 23
caactttggc attgtggaag g                                                 21

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: GAPDH R

<400> SEQUENCE: 24
gtggatgcag ggatgatgtt                                                   20

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: Universal forward primer

<400> SEQUENCE: 25
gtgtagatct caggtgggtg tcctggtata a                                      31

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: EGFP construct reverse primer

<400> SEQUENCE: 26
gtgtaagctt ctcctccccg cactcctt                                          28

<210> SEQ ID NO 27
<211> LENGTH: 29

-continued

```
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: Luciferase construct reverse primer

<400> SEQUENCE: 27
gtgtaagctt gctcctcccc gcactcctt                                        29

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: EGFP sequencing forward primer 1

<400> SEQUENCE: 28
ataaccgtat taccgccatg catta                                            25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: Luciferase sequencing forward primer 1

<400> SEQUENCE: 29
cagaacattt ctctggccta actgg                                            25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: Universal sequencing forward primer 2

<400> SEQUENCE: 30
ctctaagtgc tactgagtag aggta                                            25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      olignonucleotide
<220> FEATURE:
<223> OTHER INFORMATION: Universal sequencing forward primer 3

<400> SEQUENCE: 31
cagccacttg gagactgagg agaga                                            25

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
```

```
                              oligonucleotide
<220> FEATURE:
<223> OTHER INFORMATION: EGFP construct forward primer

<400> SEQUENCE: 32
gtgtagatct caggtgggtg tcctggtata a                                       31

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: EGFP construct reverse primer

<400> SEQUENCE: 33
gtgtaagctt ctcctccccg cactcctt                                           28

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: EGFP sequencing forward primer 1

<400> SEQUENCE: 34
ataaccgtat taccgccatg catta                                              25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: EGFP sequencing forward primer 2

<400> SEQUENCE: 35
ctctaagtgc tactgagtag aggta                                              25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: EGFP sequencing forward primer 3

<400> SEQUENCE: 36
cagccacttg gagactgagg agaga                                              25
```